US008865937B2

(12) United States Patent
Dedhiya et al.

(10) Patent No.: US 8,865,937 B2
(45) Date of Patent: Oct. 21, 2014

(54) CRYSTALLINE FORMS OF (1S,2R)-2-(AMINO METHYL)-N,N-DIETHYL-1-PHENYL CYCLOPROPANE CARBOXAMIDE

(76) Inventors: Mahendra G. Dedhiya, Pomona, NY (US); Rahul Surana, Commack, NY (US)

(*) Notice: Subject to any disclaimer, the term of this patent is extended or adjusted under 35 U.S.C. 154(b) by 562 days.

(21) Appl. No.: 12/941,293

(22) Filed: Nov. 8, 2010

(65) Prior Publication Data

US 2011/0112197 A1    May 12, 2011

Related U.S. Application Data

(60) Provisional application No. 61/258,652, filed on Nov. 6, 2009.

(51) Int. Cl.
  *C07C 233/00* (2006.01)
  *A01N 37/18* (2006.01)
  *C07C 237/24* (2006.01)
  *C07C 231/00* (2006.01)

(52) U.S. Cl.
  CPC ........... *C07C 237/24* (2013.01); *C07C 2101/02* (2013.01); *C07C 231/00* (2013.01)
  USPC .......................................... 564/164; 514/620

(58) Field of Classification Search
  USPC .......................................... 564/164; 514/620
  See application file for complete search history.

(56) References Cited

U.S. PATENT DOCUMENTS

| | | | |
|---|---|---|---|
| 4,478,836 A | 10/1984 | Mouzin et al. | |
| 5,532,244 A | 7/1996 | Wong et al. | |
| 6,028,070 A | 2/2000 | Heiligenstein | |
| 6,184,222 B1 | 2/2001 | Heiligenstein | |
| 6,602,911 B2 | 8/2003 | Kranzler et al. | |
| 6,635,675 B2 | 10/2003 | Kranzler et al. | |
| 6,699,506 B1 | 3/2004 | Paillard et al. | |
| 7,005,452 B2 | 2/2006 | Deregnaucourt et al. | |
| 2002/0010216 A1 | 1/2002 | Rogosky et al. | |
| 2003/0130353 A1 | 7/2003 | Kranzler et al. | |
| 2003/0139476 A1 | 7/2003 | Kranzler et al. | |
| 2003/0203055 A1 | 10/2003 | Rao et al. | |
| 2003/0232805 A1 | 12/2003 | Kranzler et al. | |
| 2004/0019116 A1 | 1/2004 | Kranzler et al. | |
| 2004/0034101 A1 | 2/2004 | Rao et al. | |
| 2004/0122104 A1 | 6/2004 | Hirsh et al. | |
| 2005/0032782 A1 | 2/2005 | Rao et al. | |
| 2005/0096395 A1 | 5/2005 | Rao et al. | |
| 2006/0014837 A1 | 1/2006 | Deregnaucourt et al. | |
| 2007/0015828 A1 | 1/2007 | Shah et al. | |
| 2010/0016636 A1 * | 1/2010 | Ai et al. ....................... 564/164 |

FOREIGN PATENT DOCUMENTS

| | | | |
|---|---|---|---|
| EP | 830864 A1 * | 3/1998 | |
| FR | 2759290 | 8/1998 | |
| FR | 2759906 | 8/1998 | |
| WO | 199735574 | 10/1997 | |
| WO | 0162236 | 1/2001 | |
| WO | 0126623 | 4/2001 | |
| WO | 03068211 | 8/2003 | |
| WO | 2004030633 | 4/2004 | |
| WO | 2005123706 | 12/2005 | |
| WO | WO 2008067752 A1 * | 6/2008 | |
| WO | 2008104957 | 9/2008 | |

OTHER PUBLICATIONS

Lin Ai et al., A Process for Preparing Optically Pure Milnacipran and Its Pharmaceutically Accepted Salts; Human Traslation of Chinese document—WO 2008067752 A1; pp. 1-18.*
Office Action for Canadian Patent Application No. 2,779,711 from the Canadian Intellectual Property Office dated Aug. 20, 2013.
International Search Report and Written Opinion for corresponding PCT/US2010/055783 mailed Jan. 21, 2011.
Retz, W. et al., Multiple and single dose pharmacokinetics of milnacipran in major depressive patients, FEBS Letters, vol. 5, No. 3, Sep. 1995, pp. 296-297(2).
Caron, et al., Acute electrophysiological effects of intravenous milnacipran, a new antidepressant agent, Eur Neuropsychopharmacol. Dec. 1993;3(4):493-500.
Mills, Serotonin Syndrome, A Clinical Update, Crit Care Clin. Oct. 1997;13(4):763-83.
Palazidou, et al., "Rapid Reference to Depression", Jul. 2002, 42-59.
Moret et al., Biochemical profile of midalcipran (F 2207), 1-phenyl-1-diethyl-aminocarbonyl-2-aminomethyl-cyclopropane (Z) hydrochloride, a potential fourth generation antidepressant drug 1985 Neuropharmacology 24(12): 1211-1219.
Bonnaud et al., Separation dė amides diastbrboisombes par chromatographie liquide haute performance preparative et analyse d ė bnantiomkes par chromatographie sur support chiral 1985, Journal of Chromatography, vol. 318: 398-403.
Shuto et al., Synthesis of (+)- and (-31 )-milnaciprans and their conformationally restricted analogs, Tetrahedron letters, 1996 vol. 37: 641-644.
Grard et al., Enhancement of second-migrating enantiomer peak symmetry of basic drugs by using dual-cyclodextrin system in capillary electrophoresis Electrophorasis 2000 21: 3028-3034.
Doyle et al., A New Enantioselective Synthesis of Milnacipran and an Analogue by Catalytic Asymmetric Cyclopropanation 2001, Advanced Synthesis and Catalysis, vol. 343, 299-302.
Nores et al., Cardiovascular manifestations in acute poisoning by antidepressive agents. Discussion and review of the literature 1987 Therapie 42: 555-558.

(Continued)

*Primary Examiner* — Sudhakar Katakam
*Assistant Examiner* — Kofi Adzamli

(57) ABSTRACT

The present invention relates to novel crystalline forms of (1S,2R)-2-(amino methyl)-N,N-diethyl-1-phenyl cyclopropane carboxamide. Processes for the preparation of this form, compositions containing the form, and methods of use thereof are also described.

17 Claims, 16 Drawing Sheets

(56) References Cited

OTHER PUBLICATIONS

Meador-Woodruff et al., Behavioral and cognitive toxicity related to elevated plasma tricyclic antidepressant levels J Clin Psychopharmacol. Feb. 1988;8(1):28-32.
The Diagnostic and Statistical Manual of Mental Disorders-IV(DSM-IV), 1995 A.P.A.
Deprez et al., Which bioequivalence study for a racemic drug? Application to milnacipran, Eur J Drug Metab Pharmacokinet. Apr.-Jun. 1998; 23(2): 166-71.
Spencer et al., Milnacipran. A review of its use in depression, Drugs. Sep. 1998;56(3):405-27.
Viazzo, et al., Microbiological ransformations 34: EnantioselectiveH ydrolysiso f a Key-Lactone Involved in the Synthesis of the Antidepressant Milnacipran®, Tetrahedron Letters, vol. 37, No. 26, pp. 4519-4522, 1996.
Shuto et al., Synthesis and biological activity of conformationally restricted analogues of milnacipran: (1S, 2R)-1-phenyl-2-[(R)-1-amino-2-propynyl]-N,N-diethylcyclopropanecarboxamide is a novel class of NMDA receptor channel blocker Journal of Medicinal Chemistry, 1998 vol. 41, pp. 3507-3514.
Shuto et al., Synthesis and biological activity of conformationally restricted analogs of milnacipran: (1S,2R)-1-phenyl-2-[(S)-1-aminopropyl]-N,N-diethylcyclopropanecarboxami de, an efficient noncompetitive N-methyl-D-aspartic acid receptor antagonist.Journal of Med Chem, American Chem. Society, 1996, vol. 39: 4844-4852.
Shuto et al., (1S,2R)-1-Phenyl-2-[(S)-1-aminopropyl]-N,N-diethylcyclopropanecarboxamide (PPDC), a new class of NMDA-receptor antagonist: molecular design by a novel conformational restriction strategy, Jpn J Pharmacol. Mar. 2001;85(3):207-13.
Hindmarch I., The enantiomer debate: current status and future directions. Hum Psychopharmacol. Dec. 2001;16 (S2):S101-S104.
Baldwin D.S., Unmet needs in the pharmacological management of depression Hum Psychopharmacol. Dec. 2001;16(S2):S93-S99.
Artigas, "Selective Serotonin/Noradrenaline Reuptake Inhibitors", CNS Drugs, 1995, 4, 79-89.
Preskorn, et al., "Other Antidepressants", Antidepressants: Past, Present and Future, 2004, 264-311.
Preskorn, Milnacipran: A Dual Norepinephrine and Serotonin Reuptake Pump Inhibitor, Journal of Psychiatric Practice, 2004, 10, 119-126.
Yoshida, et al., Elevation of blood pressure induced by high-dose milnacipran, Hum. Psychopharmacol. Clin. Exp., 2002, 17, 431.
Schorderet, Effets sur le systeme cardiovasculaire, Pharmacologie Des Concepts Fondamentaux Aux Applications Therapeutiques, 1992, Chapter 25, pp. 363-364.
Ener, et al., "Serotonin Syndrome and Other Serotonergic Disorders", Pain Medicine, 2003, 4, 63-74.
Kolecki, "Isolated Venlafaxine-Induced Serotonin Syndrome", J. Emerg. Med., 1997, 15, 491-493.
Hansen, et al., "Long-term antidepressive medication—an increased anesthetic risk?", Der Anaesthesist, 1990, 39, 205-210 *Surgical Medline Extract).
Thase, "Effects of Venlafaxine on Blood Pressure: A Meta-Analysis of Original Data from 3744 Patients", J. Clin. Psychiatry, 1998, 59, 502-508.
Partridge, et al., "A Depressed Myocardium", Clinical Toxicology, 2000, 38, 453-455.
Jordan, et al., Influence of sibutramine on blood pressure: evidence from placebo-controlled trials, Int J Obes (Lond). May 2005;29(5):509-16.
Birkenfeld, et al., "Paradoxical effect of sibutramine of autonomic cardiovascular regulation", Circulation, 2002, 106, 2459-2465 (Medline Extract).
Sramek, et al., "Efficacy and safety of sibutramine for weight loss in obese patients with hypertension well controlled by beta-adrenergic blocking agents: a placebo-controlled, double-blind, radomiser trial", J. Hum. Hypertens., 2002, 16, 13-19 (Medline Extract).
Szabadi, et al., "The human pharmacology of reboxetine", Hum. Psychopharmacol., 1998, Suppl. 1, S3-S12 (Excerpta Medica Extract).
Middleton, et al., "Evidence that imipramine-induced postural hypotension may be centrally mediated", Hum. Psychopharmacol., 1998, 3, 181-190 (Excerpta Medica Extract).
Robinson, "Antidepressant Psychopharmacology: Current Limitations and Future Directions", Primary Psychiatry, 2003, 10, 43-49.

* cited by examiner

CRYSTALLINE FORMS OF (1S,2R)-2-(AMINO METHYL)-N,N-DIETHYL-1-PHENYL CYCLOPROPANE CARBOXAMIDE

This application claims the benefit of U.S. Provisional Application No. 61/258,652, filed on Nov. 6, 2009, the entire contents of which are hereby incorporated by reference.

FIELD OF THE INVENTION

The present invention relates to novel crystalline forms of (1S,2R)-2-(amino methyl)-N,N-diethyl-1-phenyl cyclopropane carboxamide. Processes for the preparation of these forms, compositions containing these forms, and methods of using these forms are also described.

BACKGROUND OF THE INVENTION

U.S. Pat. No. 7,005,452 discloses novel therapeutics that are useful in the treatment of disorders that can be managed by inhibition of norepinephrine (NE) and serotonin (5-HT) reuptake, for example, anxiety disorders and depression (e.g., major depressive disorder). One compound disclosed in the '452 patent which is believed to be particularly effective for treating these types of disorders is (1S,2R)-2-(amino methyl)-N,N-diethyl-1-phenyl cyclopropane carboxamide. The structural formula of (1S,2R)-2-(amino methyl)-N,N-diethyl-1-phenyl cyclopropane carboxamide is:

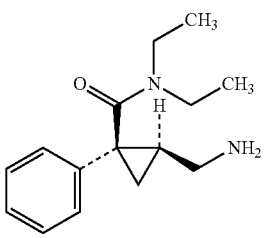

The entire contents of the '452 patent are hereby incorporated by reference in their entirety.

The present invention relates to the solid state physical properties of (1S,2R)-2-(amino methyl)-N,N-diethyl-1-phenyl cyclopropane carboxamide. These properties may be influenced by controlling the conditions under which this compound is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state physical property of a pharmaceutical compound is its rate of dissolution in solution which may have therapeutic consequences since it imposes an upper limit on the rate at which an orally-administered active ingredient may reach the patient's bloodstream. The solid state form of a compound may also affect its behavior on compaction and its storage stability.

These practical physical characteristics are influenced by the conformation and orientation of molecules in the unit cell, which defines a particular crystalline or polymorphic form of a substance. The crystalline or polymorphic form may give rise to thermal behavior different from that of the amorphous material or another crystalline or polymorphic form. Thermal behavior is measured in the laboratory by such techniques as capillary melting point, thermogravimetric analysis (TGA) and differential scanning calorimetry (DSC) and may be used to distinguish some crystalline or polymorphic forms from others. A particular crystalline or polymorphic form may also give rise to distinct spectroscopic properties that may be detectable by X-ray powder diffraction (XRPD), solid state nuclear magnetic resonance (NMR) spectrometry, Raman spectroscopy and infrared (IR) spectrometry.

In deciding which polymorph or crystalline form is preferable, the numerous properties of the polymorphs or crystalline forms must be compared and the preferred polymorph or crystalline form chosen based on the many physical property variables. It is entirely possible that one polymorph or crystalline form can be preferable in some circumstances in which certain aspects, such as ease of preparation, stability, etc., are deemed to be critical. In other situations, a different crystalline form or polymorph may be preferred for greater solubility and/or superior pharmacokinetics.

The discovery of new crystalline or polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. New crystalline forms of (1S,2R)-2-(amino methyl)-N,N-diethyl-1-phenyl cyclopropane carboxamide have now been discovered.

SUMMARY OF THE INVENTION

The present invention relates to novel crystalline forms of (1S,2R)-2-(amino methyl)-N,N-diethyl-1-phenyl cyclopropane carboxamide. Processes for the preparation of these forms, compositions containing these forms, and methods of use thereof are also described.

In some embodiments, the present invention relates to pharmaceutical composition comprising the crystalline form of (1S,2R)-2-(amino methyl)-N,N-diethyl-1-phenyl cyclopropane carboxamide and a pharmaceutically acceptable carrier.

In some embodiments, the present invention relates to a method for treating and/or preventing a disorder than can be managed by inhibition of serotonin (5-HT) and norepinephrine (NE) reuptake (e.g., major depressive disorder) comprising administering to a patient in need thereof, an effective amount of a pharmaceutical composition that comprises the crystalline form of (1S,2R)-2-(amino methyl)-N,N-diethyl-1-phenyl cyclopropane carboxamide.

In some embodiments, the present invention relates to a method for preparing the crystalline form of (1S,2R)-2-(amino methyl)-N,N-diethyl-1-phenyl cyclopropane carboxamide.

DETAILED DESCRIPTION OF THE INVENTION

Novel crystalline forms of (1S,2R)-2-(amino methyl)-N,N-diethyl-1-phenyl cyclopropane carboxamide, as well as compositions containing these forms, methods of treating using these crystalline forms, and methods for preparing these forms, are provided herein.

U.S. Pat. No. 7,005,452 discloses methods-of-treatment using (1S,2R)-2-(amino methyl)-N,N-diethyl-1-phenyl cyclopropane carboxamide. In addition, the '452 patent teaches that (1S,2R)-2-(amino methyl)-N,N-diethyl-1-phenyl cyclopropane carboxamide is prepared using the process disclosed in U.S. Pat. No. 4,478,836. This process includes a final precipitation step that occurs in ethanol and ethyl ether. The crystalline form of (1S,2R)-2-(amino methyl)-N,N-diethyl-1-phenyl cyclopropane carboxamide that forms in the prior art mixture of ethanol and ethyl ether is provided in Example 1 of the present application. This crystalline form is hereinafter referred to as "Form A."

Figure 1:
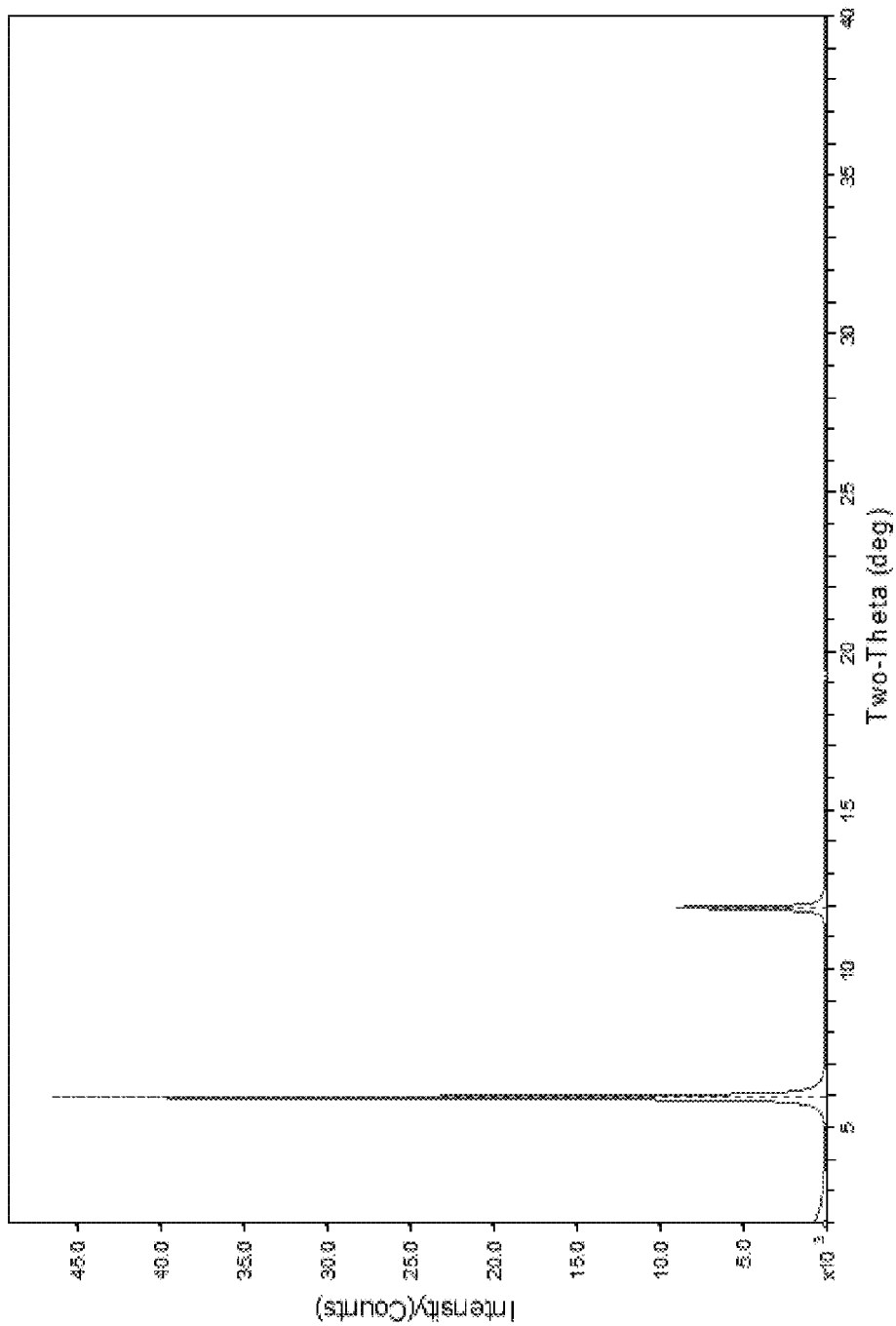
FIG. 1 shows the X-ray powder diffraction (XRPD) pattern of Form A (1S,2R)-2-(amino methyl)-N,N-diethyl-1-phenyl cyclopropane carboxamide.

The X-ray powder diffraction pattern for Form A is provided in FIG. 1. Form A displays an X-ray powder diffraction pattern having characteristic peaks at 5.9, 11.9, 24.0, 30.1 and 36.3 degrees 2θ.

Inventive Crystalline Forms

In some embodiments, the present invention provides a crystalline form of (1S,2R)-2-(amino methyl)-N,N-diethyl-1-phenyl cyclopropane carboxamide which has an X-ray powder diffraction (XRPD) pattern comprising one or more peaks as provided in Table 2. As used herein, unless otherwise indicated, the phrase "one or more peaks" should be understood to be inclusive of (i) crystalline forms that have XRD peaks at every peak value recited after this phrase, (ii) crystalline forms that have an XRD peak at only one of the peak values recited after this phrase, as well (iii) crystalline forms that have XRD peaks at two or more (e.g., three or more, four or more, five or more, six or more, or even seven or more) of the peak values recited after this phrase.

TABLE 2

| 2-Theta (°) | d(Å) |
| --- | --- |
| 6.0 | 14.7 |
| 12.0 | 7.4 |
| 14.2 | 6.2 |
| 16.6 | 5.4 |
| 17.4 | 5.1 |
| 18.2 | 4.9 |
| 20.1 | 4.4 |
| 21.2 | 4.2 |
| 21.7 | 4.1 |
| 22.5 | 4.0 |
| 24.1 | 3.7 |
| 24.6 | 3.6 |
| 29.2 | 3.1 |
| 30.2 | 3.0 |
| 30.7 | 2.9 |
| 32.7 | 2.7 |
| 35.3 | 2.5 |
| 36.4 | 2.5 |

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0 and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 20.1 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 12.0, about 20.1 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 20.1 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 17.4 and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 17.4 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 17.4, about 20.1 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 12.0, about 17.4, about 20.1 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 17.4, and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 17.4, and about 20.1±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 20.1 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 12.0, about 17.4, and about 20.1±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 17.4, and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 17.4, about 20.1 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 18.2 and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 12.0, about 18.2 and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 18.2 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 12.0, about 18.2 and about 22.5±0.2 degrees 2θ.

In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 18.2 and about 22.5±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 18.2 and about 20.1±0.2 degrees 2θ. In some embodiments, a crystalline form of (1S,2R)-2-(amino methyl)-N,N-diethyl-1-phenyl cyclopropane carboxamide is provided, wherein the crystalline form has an XRPD pattern comprising peaks at about 6.0, about 12.0, about 17.4, about 18.2, about 20.1 and about 22.5±0.2 degrees 2θ.

In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.1, about 22.5, about 24.6, about 29.2, about 30.7, about 32.7, and about 35.3±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.1, about 22.5, about 24.6, about 30.7, and about 32.7±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.1, and about 22.5±0.2 degrees 2θ.

Figure 2:
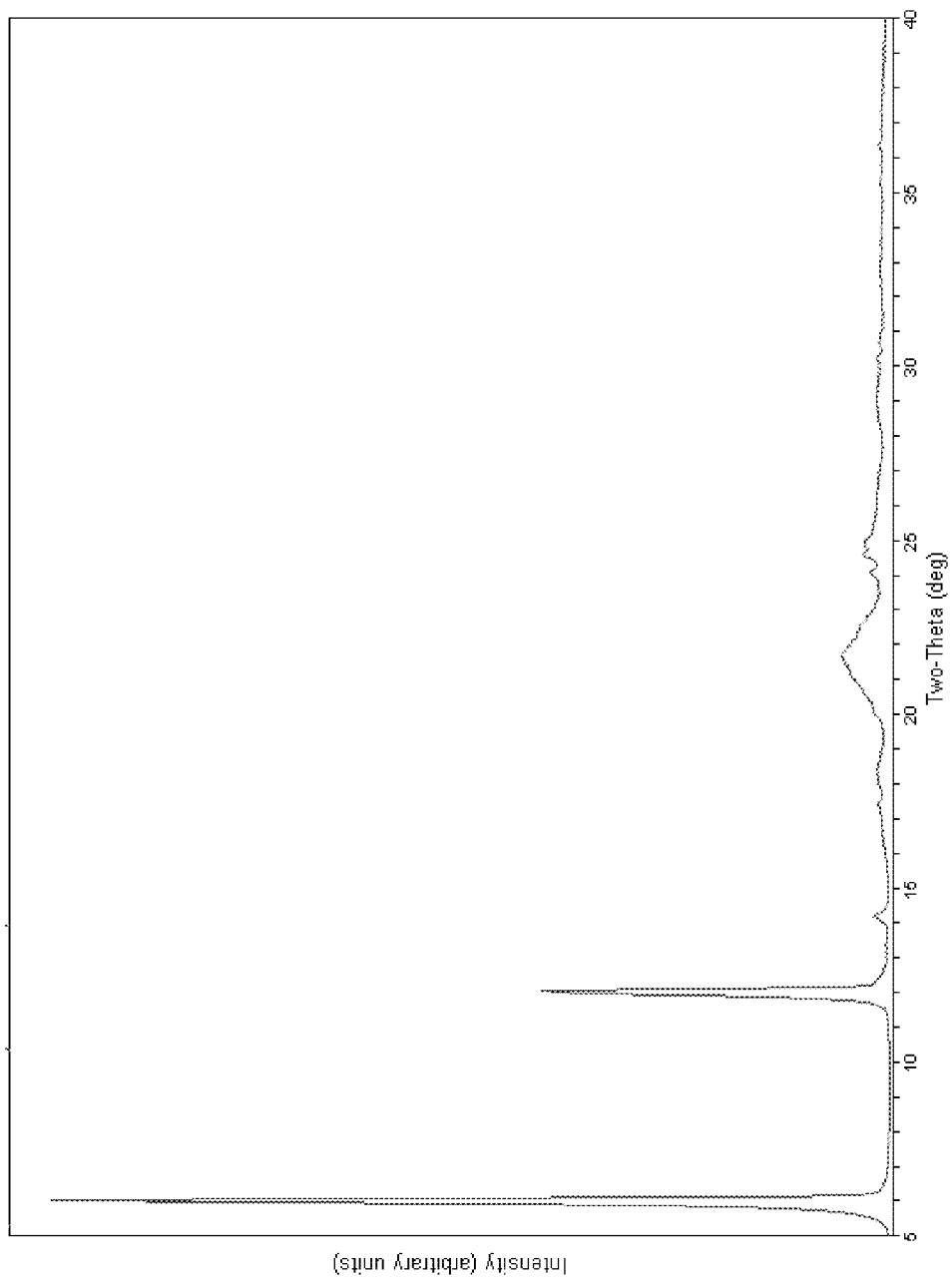
FIG. 2 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 2. With respect to the term "substantially," one skilled in the art would understand that relative XRD intensities of the peaks can vary, depending upon the sample preparation technique, the sample mounting procedure and the particular instrument employed. Moreover, instrument variation and other factors can affect the 2θ values. Therefore, the XRD peak assignments can vary by plus or minus about 0.2 degrees 2θ.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 2, e.g., one or more peaks at about 2.7, about 3.1, about 3.6, about 4.0, about 4.4 and/or about 5.1 Å±0.2 angstroms. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks at about 4.0, about 4.4, and about 5.1 Å±0.2 angstroms.

Figure 14:
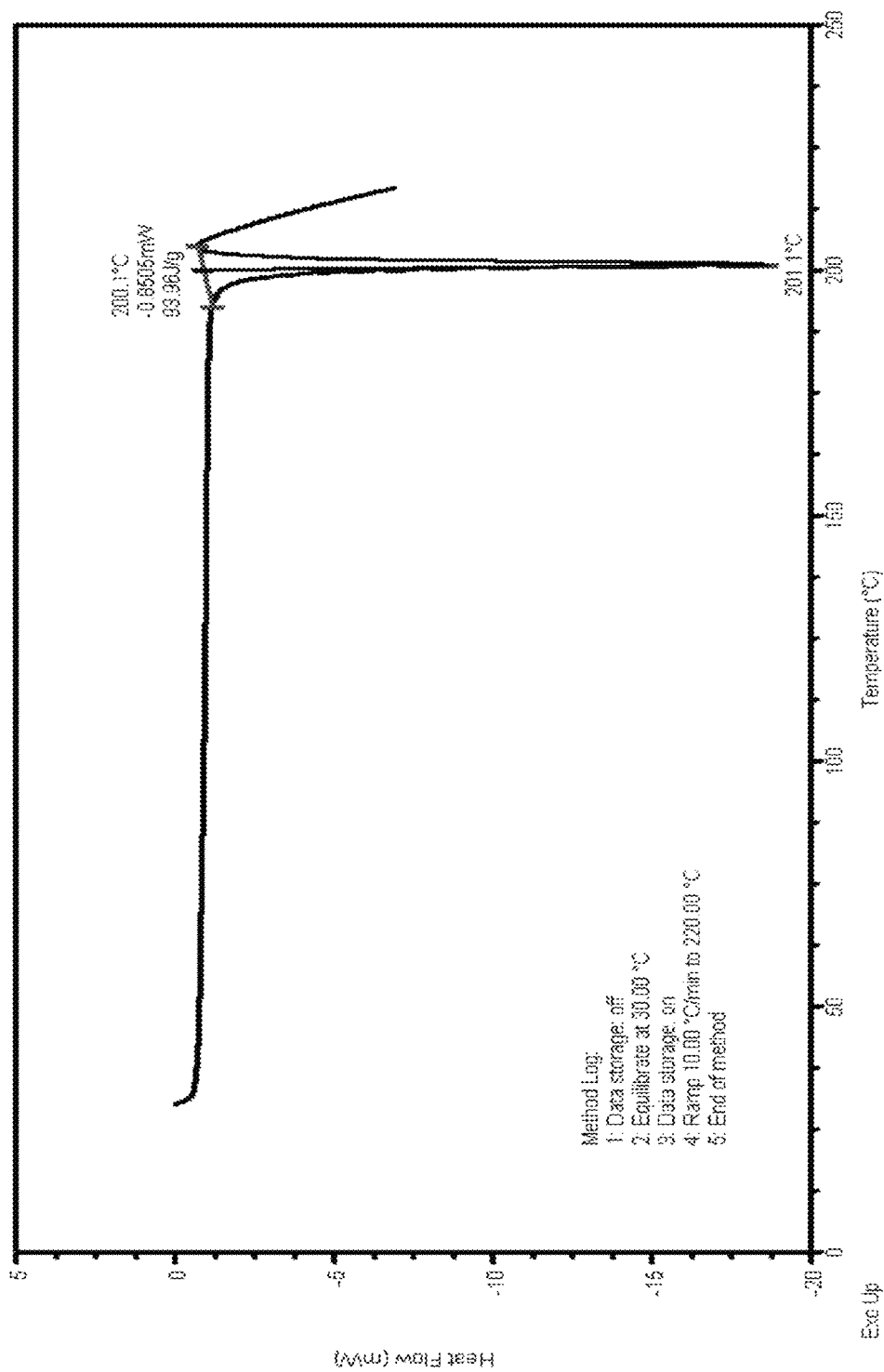
FIG. 14 shows the differential scanning calorimetry trace for a crystalline form of (1S,2R)-2-(amino methyl)-N,N-diethyl-1-phenyl cyclopropane carboxamide in accordance with an embodiment of the invention.

In some embodiments, the crystalline form can also be identified by its characteristic differential scanning calorimetry (DSC) trace, e.g., a DSC trace substantially as shown in FIG. 14. In some embodiments, the crystalline form is characterized by a DSC trace showing a first endothermic transition with an onset at about 200° C.

Figure 15:
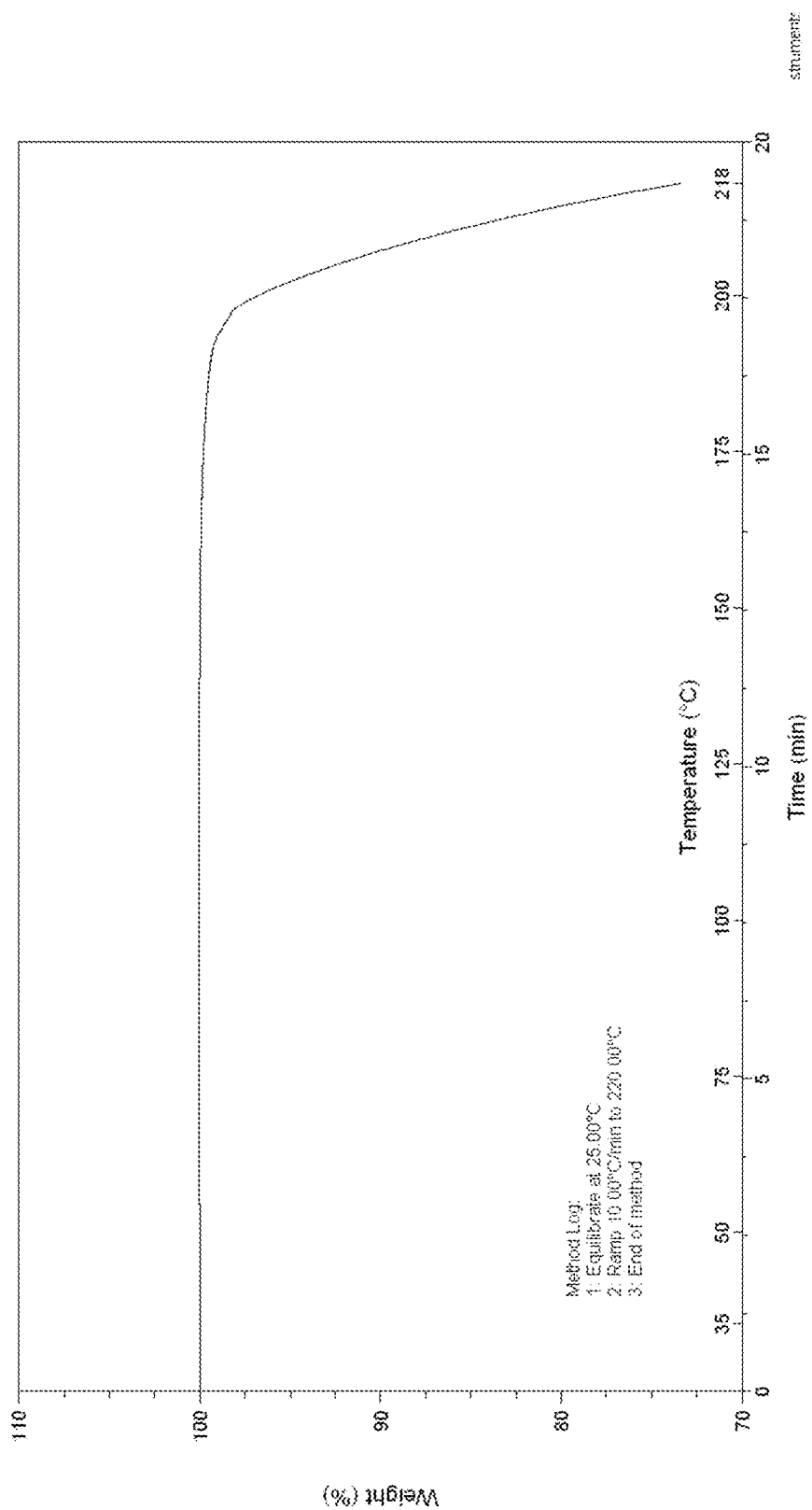
FIG. 15 shows the thermogravimetric analysis for a crystalline form of (1S,2R)-2-(amino methyl)-N,N-diethyl-1-phenyl cyclopropane carboxamide in accordance with an embodiment of the invention.

The thermogravimetric analysis (TGA) trace for a crystalline form of (1S,2R)-2-(amino methyl)-N,N-diethyl-1-phenyl cyclopropane carboxamide is shown in FIG. 15.

In some embodiments, a crystalline form of (1S,2R)-2-(amino methyl)-N,N-diethyl-1-phenyl cyclopropane carboxamide is provided, wherein the crystalline form is characterized by a TGA trace substantially as shown in FIG. 15.

Figure 16:
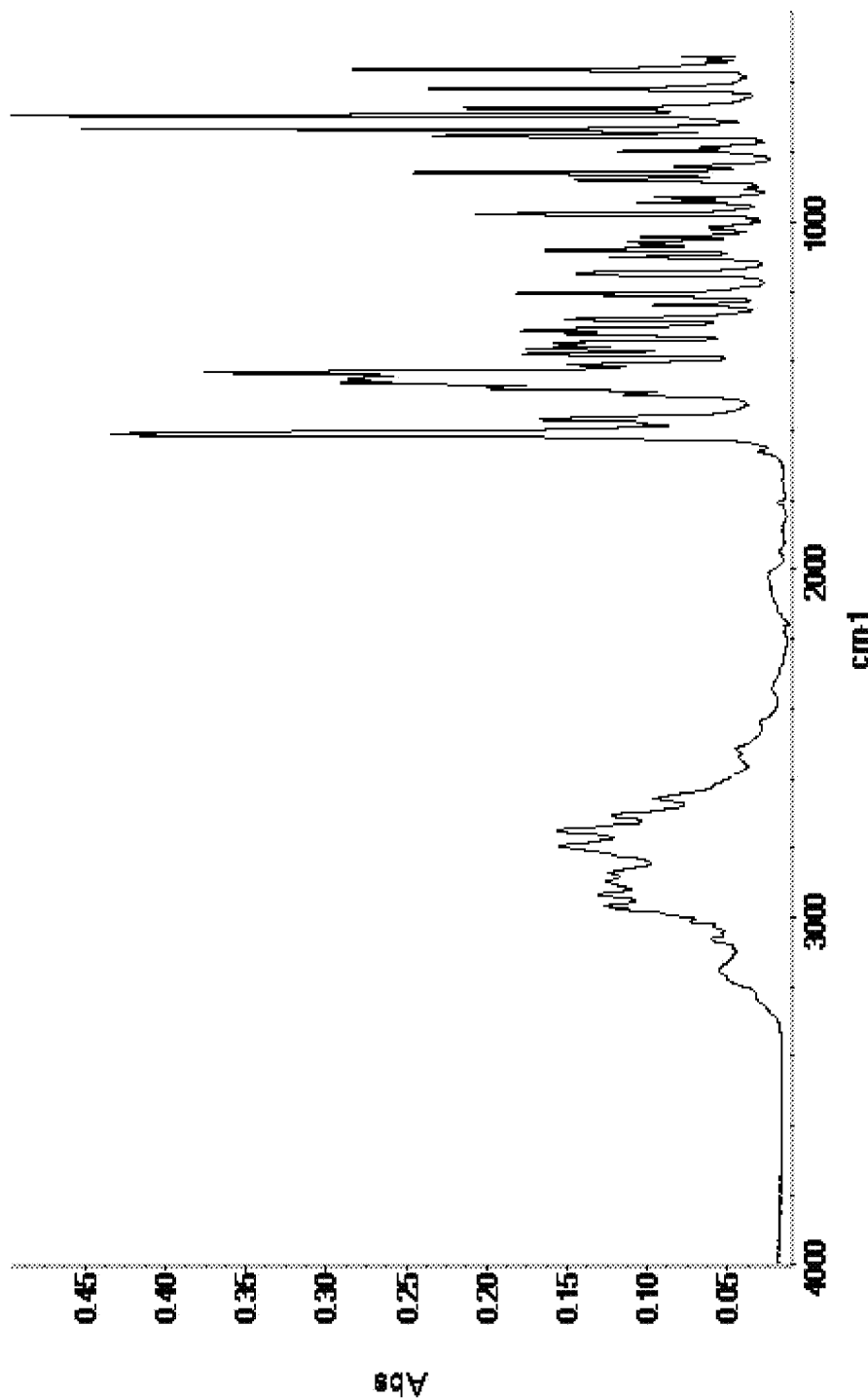
FIG. 16 shows the Raman spectrum of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a Raman spectrum substantially as shown in FIG. 16. In some embodiments, a crystalline form of (1S,2R)-2-(amino methyl)-N,N-diethyl-1-phenyl cyclopropane carboxamide is provided, wherein the crystalline form is characterized by a Raman spectrum having one or more of the peaks substantially as shown in Table 14.

TABLE 14

| Peak Position | Peak Intensity |
| --- | --- |
| 564 | 0.3 |
| 621 | 0.2 |
| 676 | 0.2 |
| 695 | 0.5 |
| 735 | 0.5 |
| 754 | 0.2 |
| 799 | 0.1 |
| 844 | 0.1 |
| 863 | 0.2 |
| 881 | 0.1 |
| 932 | 0.1 |
| 945 | 0.1 |
| 980 | 0.2 |
| 1014 | 0.1 |
| 1044 | 0.1 |
| 1059 | 0.1 |
| 1083 | 0.2 |
| 1101 | 0.1 |
| 1151 | 0.1 |
| 1208 | 0.2 |
| 1241 | 0.1 |
| 1281 | 0.2 |
| 1314 | 0.2 |
| 1323 | 0.2 |
| 1350 | 0.2 |
| 1366 | 0.2 |
| 1381 | 0.2 |
| 1411 | 0.1 |
| 1435 | 0.4 |
| 1453 | 0.3 |
| 1465 | 0.3 |
| 1479 | 0.2 |
| 1497 | 0.1 |
| 1568 | 0.2 |
| 1612 | 0.4 |
| 2658 | 0.1 |
| 2707 | 0.1 |
| 2750 | 0.2 |
| 2797 | 0.2 |
| 2935 | 0.1 |
| 2965 | 0.1 |

In some embodiments, a crystalline form of (1S,2R)-2-(amino methyl)-N,N-diethyl-1-phenyl cyclopropane carboxamide is provided, wherein the crystalline form is characterized by a Raman spectrum comprising characteristic peaks at about 695, about 735, and about 1435 cm$^{-1}$.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 3.

TABLE 3

| 2-Theta (°) | d(Å) |
| --- | --- |
| 6.0 | 14.8 |
| 12.0 | 7.4 |
| 14.2 | 6.2 |
| 16.9 | 5.2 |
| 17.4 | 5.1 |
| 18.4 | 4.8 |
| 20.1 | 4.4 |
| 21.2 | 4.2 |
| 21.7 | 4.1 |
| 22.5 | 3.9 |
| 24.0 | 3.7 |
| 24.6 | 3.6 |
| 28.8 | 3.1 |
| 30.8 | 2.9 |
| 31.8 | 2.8 |
| 32.9 | 2.7 |
| 35.3 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 16.9, about 17.4, about 20.1, about 22.5, about 24.6, about 30.8, about 32.9, and about 35.3±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 16.9, about 20.1, about 22.5, about 24.6, and about 35.3±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 20.1, about 22.5, and about 24.6±0.2 degrees 2θ.

Figure 3:
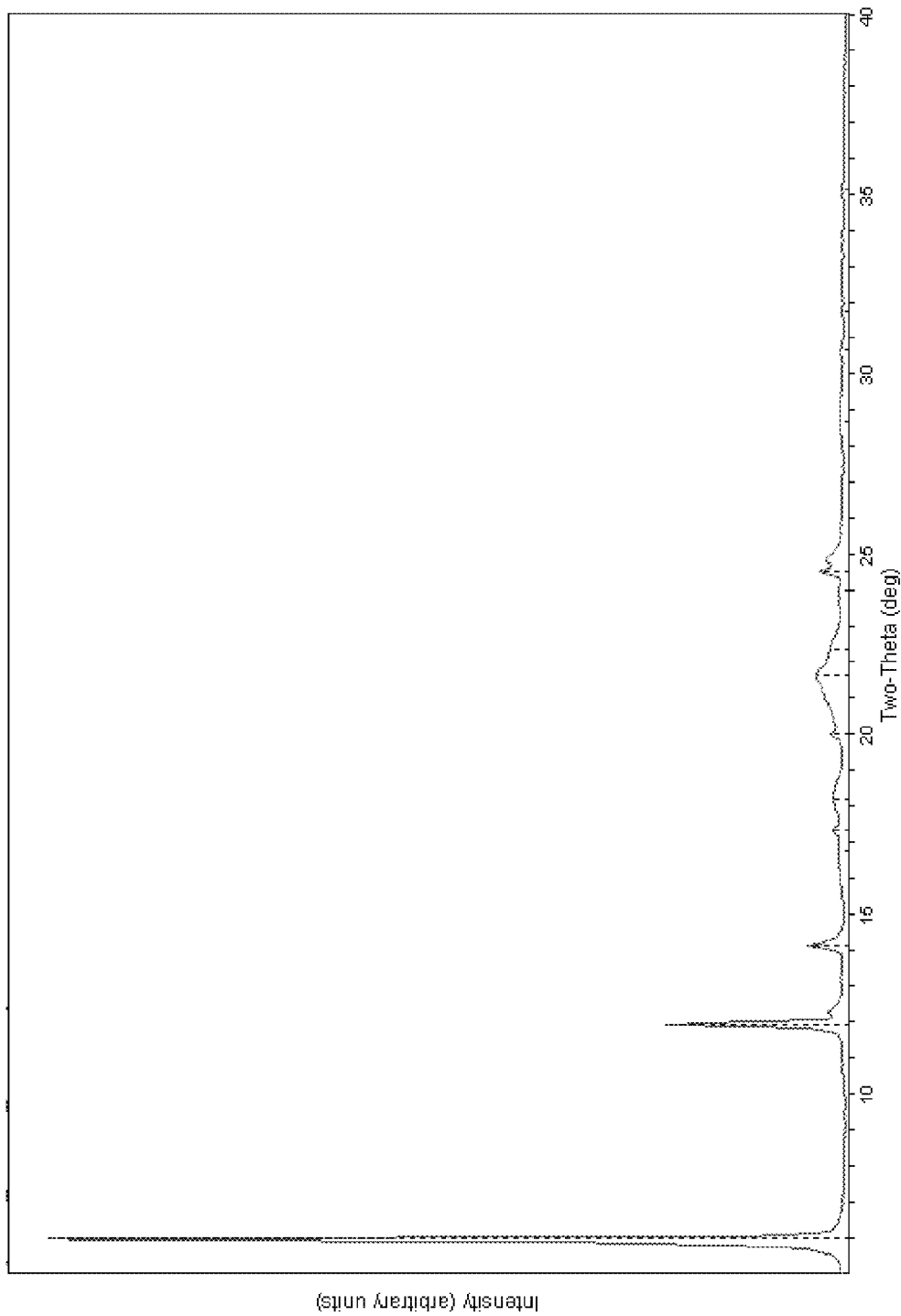
FIG. 3 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 3.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 3. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 3.6, about 3.9, and about 4.4 Å+0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 4.

TABLE 4

| 2-Theta (°) | d(Å) |
| --- | --- |
| 5.9 | 14.8 |
| 12.0 | 7.4 |
| 14.2 | 6.2 |
| 16.8 | 5.3 |
| 17.4 | 5.1 |
| 18.3 | 4.8 |
| 20.2 | 4.4 |
| 21.8 | 4.1 |

TABLE 4-continued

| 2-Theta (°) | d(Å) |
|---|---|
| 24.1 | 3.7 |
| 24.6 | 3.6 |
| 30.1 | 3.0 |
| 31.8 | 2.8 |
| 36.4 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.2, and about 24.6±0.2 degrees 2θ.

Figure 4:
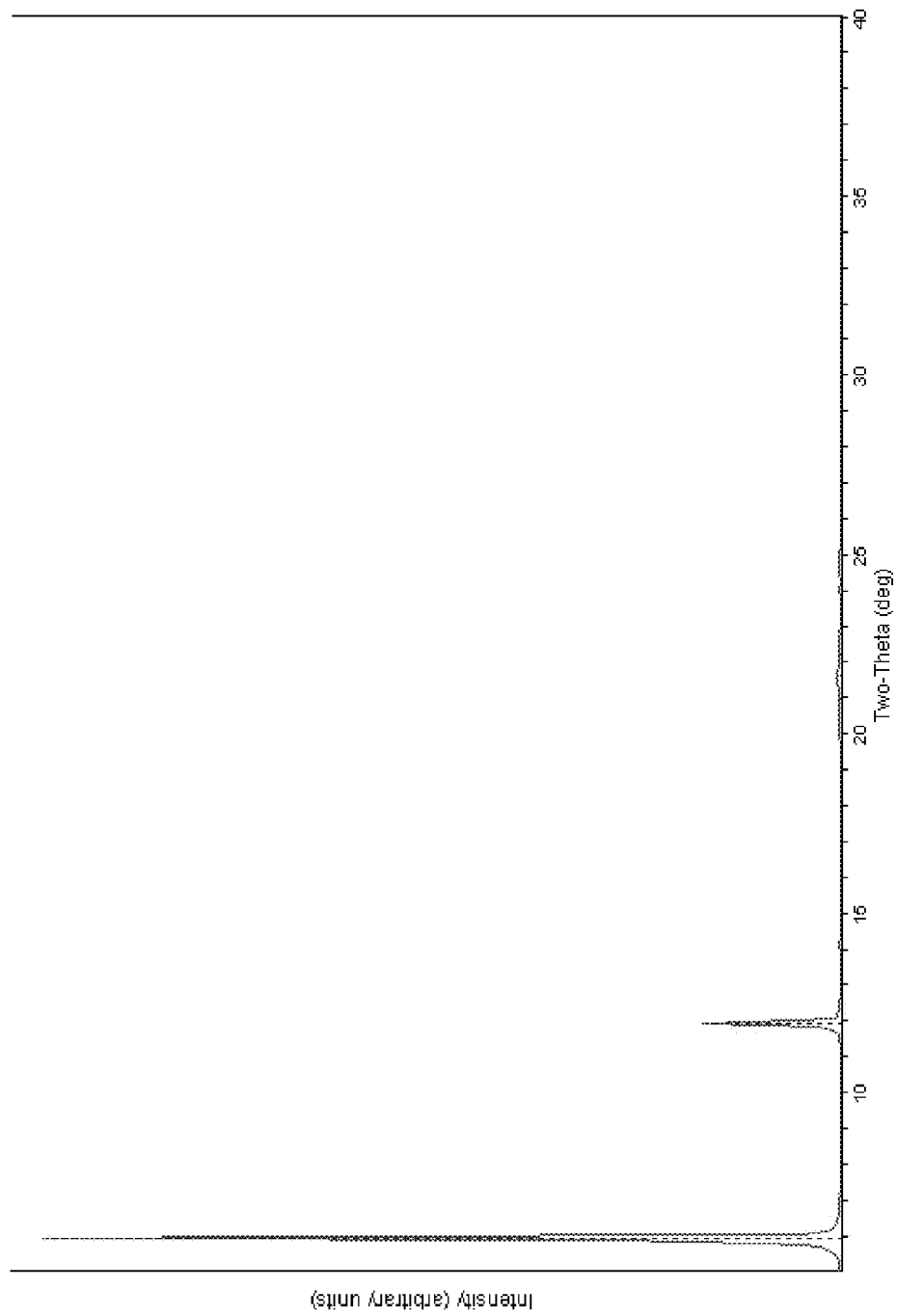
FIG. 4 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 4.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 4. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 3.6, about 4.4, and about 5.1 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 5.

TABLE 5

| 2-Theta (°) | d(Å) |
|---|---|
| 5.9 | 14.9 |
| 12.0 | 7.4 |
| 14.2 | 6.2 |
| 16.6 | 5.3 |
| 17.4 | 5.1 |
| 18.2 | 4.9 |
| 18.5 | 4.8 |
| 20.1 | 4.4 |
| 21.0 | 4.2 |
| 21.8 | 4.1 |
| 22.5 | 3.9 |
| 24.1 | 3.7 |
| 24.6 | 3.6 |
| 28.6 | 3.1 |
| 29.2 | 3.1 |
| 30.8 | 2.9 |
| 31.8 | 2.8 |
| 32.7 | 2.7 |
| 35.5 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.1, about 22.5, about 24.6, and about 32.7±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 17.4, about 20.1, and about 22.5±0.2 degrees 2θ.

Figure 5:
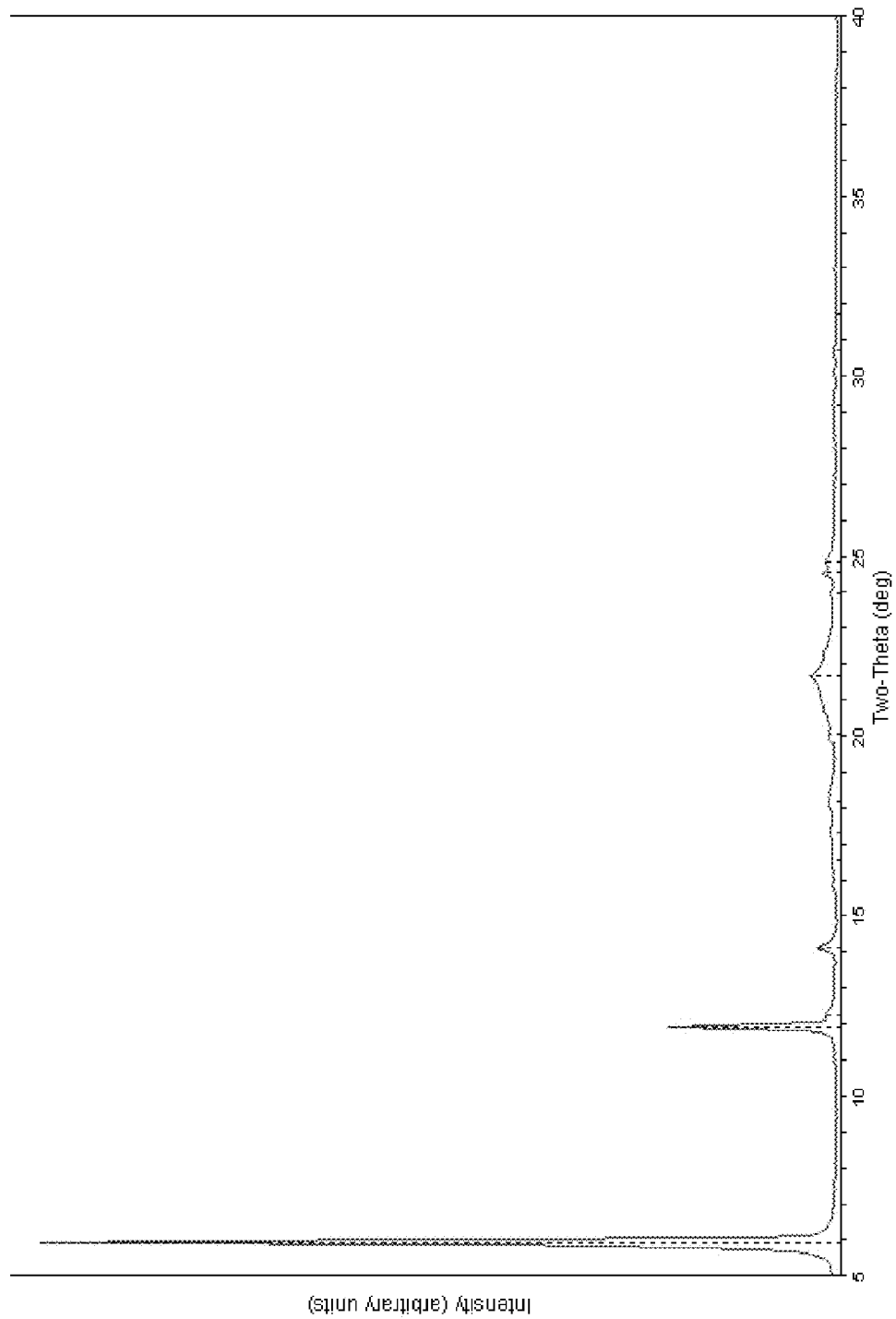
FIG. 5 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 5.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 5. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 3.9, about 4.4, and about 5.1 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 6.

TABLE 6

| 2-Theta (°) | d(Å) |
|---|---|
| 5.9 | 14.6 |
| 12.0 | 7.4 |
| 13.3 | 6.7 |
| 14.2 | 6.2 |
| 16.4 | 5.4 |
| 17.4 | 5.1 |
| 18.2 | 4.9 |
| 18.6 | 4.8 |
| 21.6 | 4.1 |
| 24.0 | 3.7 |
| 24.6 | 3.6 |
| 24.9 | 3.6 |
| 26.7 | 3.3 |
| 28.8 | 3.1 |
| 35.8 | 2.5 |
| 37.9 | 2.4 |

In some embodiments, a crystalline form of (1S,2R)-2-(amino methyl)-N,N-diethyl-1-phenyl cyclopropane carboxamide is provided having an XRPD pattern comprising one or more peaks at about 17.4, about 24.0, about 24.6, and about 37.9±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 17.4 and at about 24.6±0.2 degrees 2θ.

Figure 6:
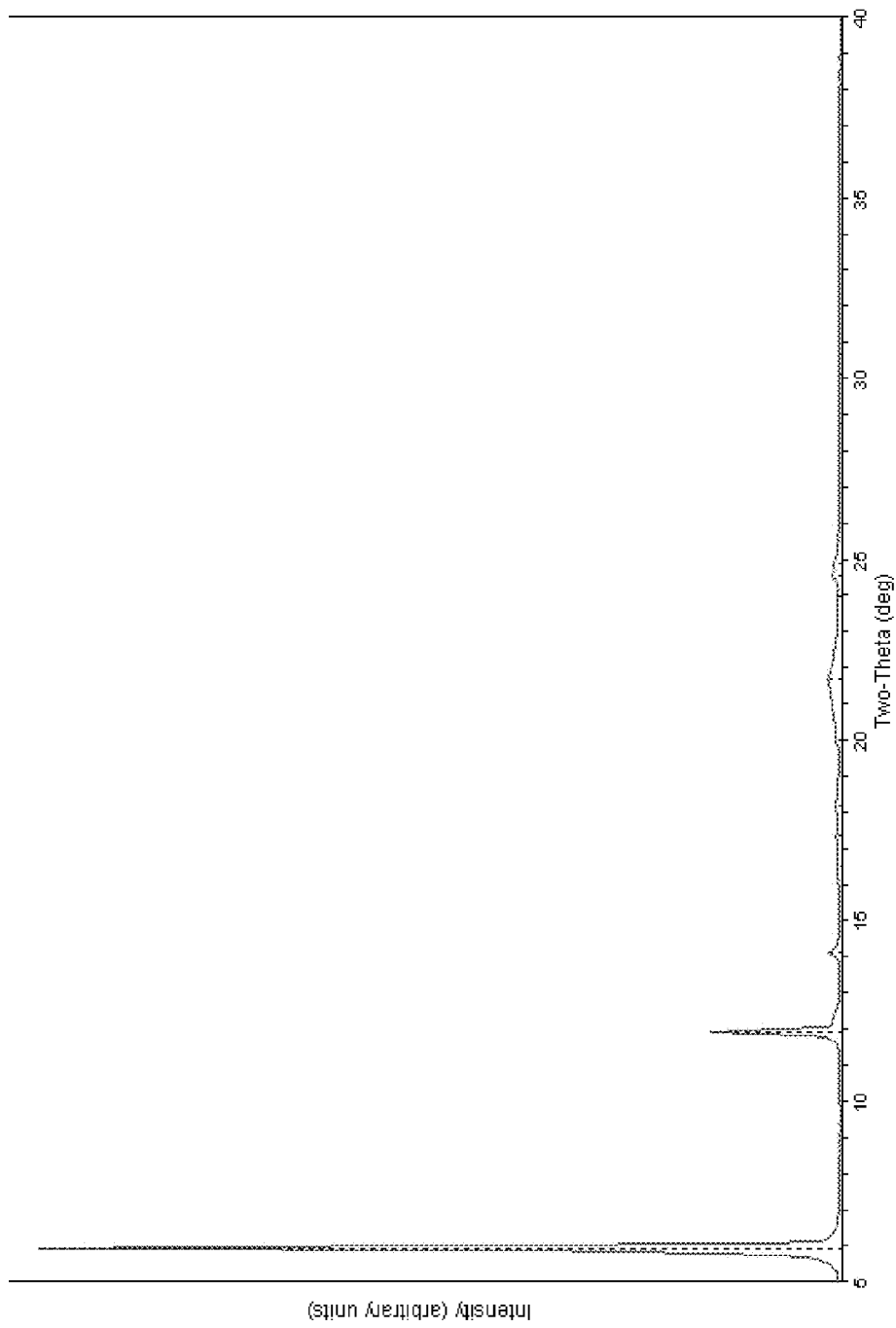
FIG. 6 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 6.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 6. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 5.1, about 3.7, about 3.6, and 2.4 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 7.

TABLE 7

| 2-Theta (°) | d(Å) |
|---|---|
| 5.9 | 14.9 |
| 12.0 | 7.4 |
| 14.2 | 6.2 |
| 16.7 | 5.3 |
| 17.4 | 5.1 |
| 18.3 | 4.9 |
| 20.0 | 4.4 |
| 21.6 | 4.1 |
| 22.2 | 4.0 |
| 24.6 | 3.6 |
| 24.0 | 3.7 |
| 28.5 | 3.1 |
| 29.0 | 3.1 |
| 30.2 | 3.0 |
| 30.7 | 2.9 |
| 36.4 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 17.4, about 24.6, and about 28.5±0.2 degrees 2θ.

Figure 7:
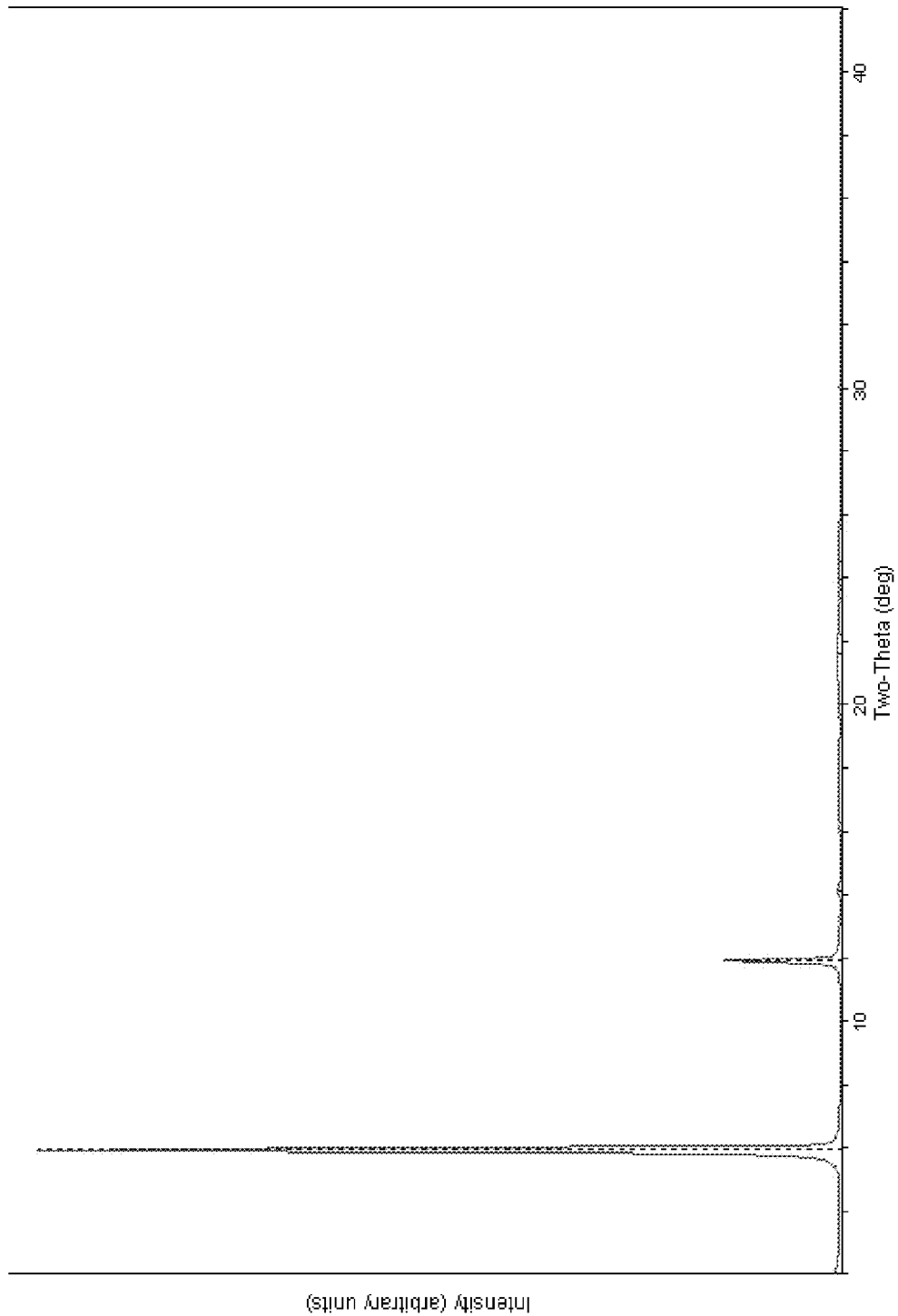
FIG. 7 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 7.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 7. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 5.1, about 3.6, and about 3.1 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 8.

TABLE 8

| 2-Theta (°) | d(Å) |
|---|---|
| 6.0 | 14.8 |
| 12.0 | 7.4 |
| 12.3 | 7.2 |
| 13.3 | 6.7 |
| 14.2 | 6.2 |
| 16.8 | 5.3 |
| 17.5 | 5.1 |
| 18.5 | 4.8 |
| 20.1 | 4.4 |
| 21.2 | 4.2 |
| 21.7 | 4.1 |
| 22.5 | 4.0 |
| 23.6 | 3.8 |
| 24.0 | 3.7 |
| 24.6 | 3.6 |
| 24.9 | 3.6 |
| 25.0 | 3.6 |
| 29.2 | 3.1 |
| 30.2 | 3.0 |
| 30.8 | 2.9 |
| 31.8 | 2.8 |
| 32.6 | 2.7 |
| 35.0 | 2.6 |
| 35.3 | 2.5 |
| 36.4 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 12.3, about 16.8, about 17.5, about 20.1, about 22.5, about 24.6, about 29.2, about 30.8, about 32.6, and about 35.0±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 16.8, about 17.5, about 20.1, about 22.5, and about 24.6±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 17.5, about 20.1, and about 22.5±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 20.1, and about 22.5±0.2 degrees 2θ.

Figure 8:
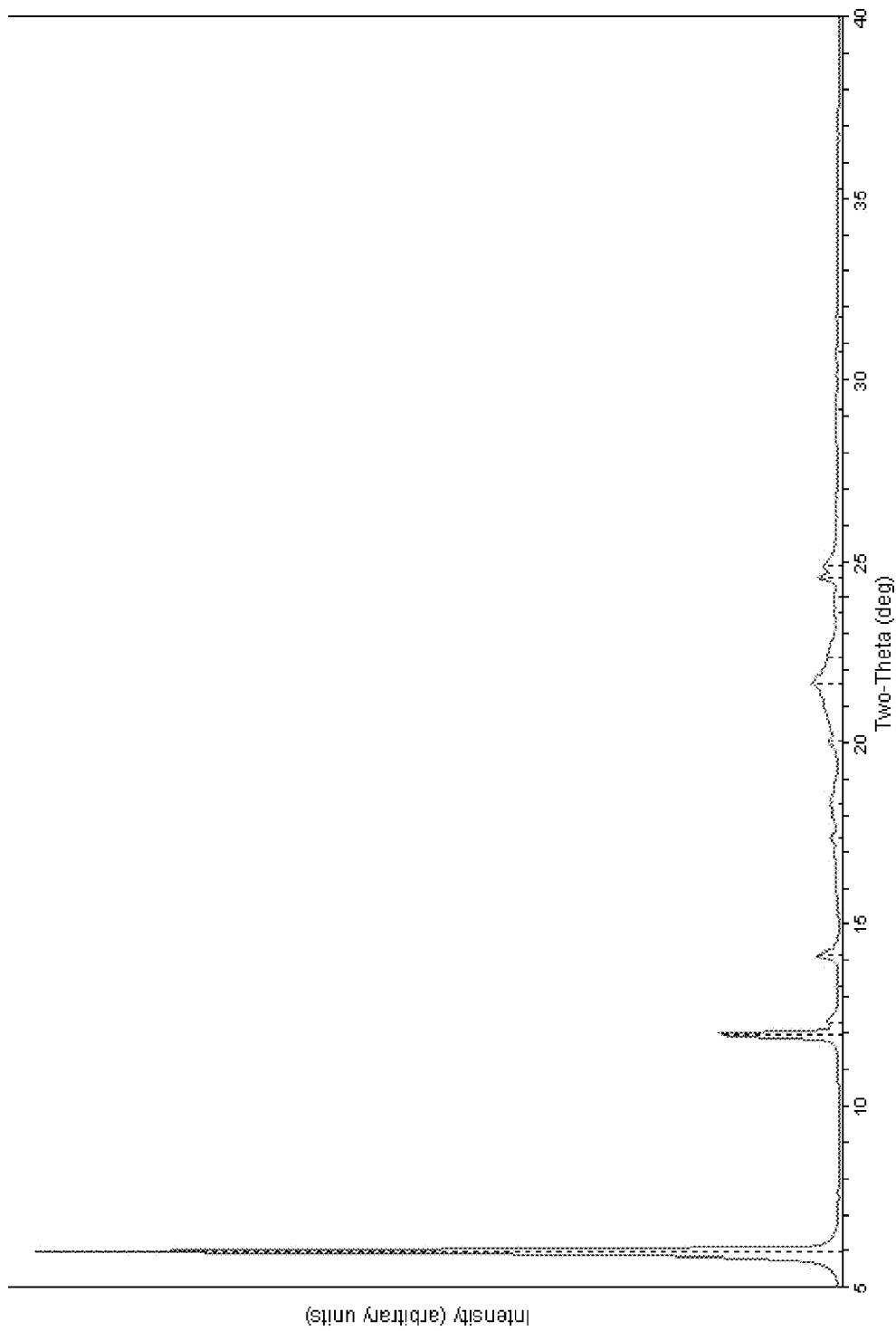
FIG. 8 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 8.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 8. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 7.2, about 4.4, and about 4.0 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 9.

TABLE 9

| 2-Theta (°) | d(Å) |
|---|---|
| 6.0 | 14.8 |
| 12.0 | 7.4 |
| 12.4 | 7.2 |
| 13.3 | 6.6 |
| 14.2 | 6.2 |
| 16.8 | 5.3 |
| 17.5 | 5.1 |
| 18.2 | 4.9 |
| 20.1 | 4.4 |
| 20.8 | 4.3 |
| 21.1 | 4.2 |
| 21.8 | 4.1 |
| 22.4 | 4.0 |
| 24.1 | 3.7 |
| 24.6 | 3.6 |
| 25.0 | 3.6 |
| 26.8 | 3.3 |
| 28.8 | 3.1 |
| 30.8 | 2.9 |

TABLE 9-continued

| 2-Theta (°) | d(Å) |
|---|---|
| 31.8 | 2.8 |
| 32.6 | 2.7 |
| 35.3 | 2.5 |
| 37.3 | 2.4 |

In some embodiments, a crystalline form of (1S,2R)-2-(amino methyl)-N,N-diethyl-1-phenyl cyclopropane carboxamide is provided having an XRPD pattern comprising one or more peaks at about 12.4, about 16.8, about 17.5, about 20.1, about 22.4, about 24.6, about 30.8, about 32.6, about 35.3, and about 37.3±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.4, about 20.1, about 22.4, and about 24.6±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.4, about 20.1, and about 22.4±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4, about 20.1, and about 22.4±0.2 degrees 2θ.

Figure 9:
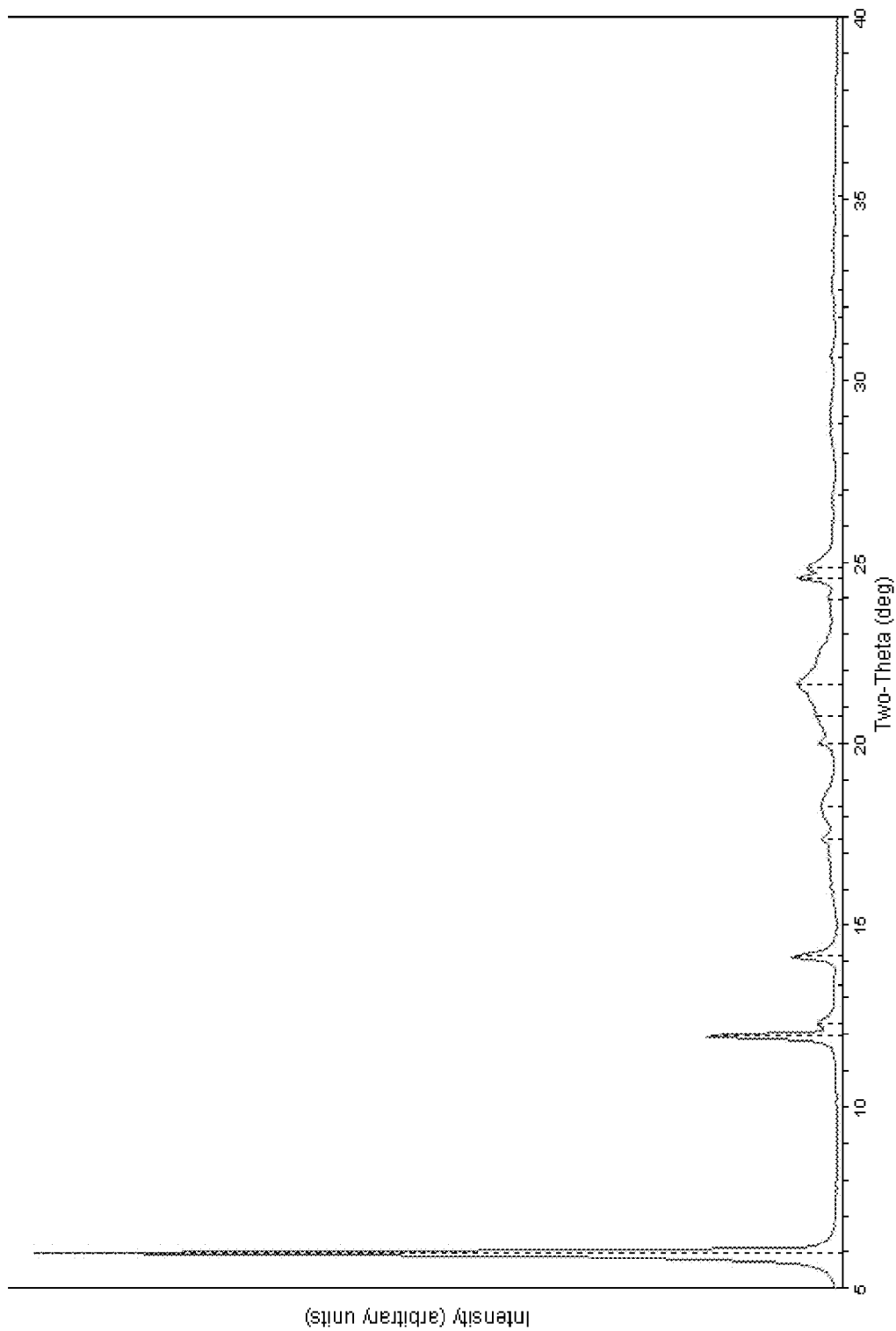
FIG. 9 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 9.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 9. In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising d spacing peaks at about 7.2, about 4.4, and about 4.0 Å±0.2 angstroms.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 10.

TABLE 10

| 2-Theta (°) | d(Å) |
|---|---|
| 6.0 | 14.8 |
| 12.0 | 7.4 |
| 12.4 | 7.2 |
| 13.3 | 6.6 |
| 14.2 | 6.2 |
| 16.7 | 5.3 |
| 17.5 | 5.1 |
| 18.2 | 4.9 |
| 20.1 | 4.4 |
| 21.2 | 4.2 |
| 21.8 | 4.1 |
| 22.5 | 3.9 |
| 24.0 | 3.7 |
| 24.7 | 3.6 |
| 25.0 | 3.6 |
| 26.6 | 3.3 |
| 28.9 | 3.1 |
| 30.8 | 2.9 |
| 31.8 | 2.8 |

TABLE 10-continued

| 2-Theta (°) | d(Å) |
|---|---|
| 35.3 | 2.5 |
| 37.2 | 2.4 |

In some embodiments, a crystalline form of (1S,2R)-2-(amino methyl)-N,N-diethyl-1-phenyl cyclopropane carboxamide is provided having an XRPD pattern comprising one or more peaks at about 12.4, about 17.5, about 20.1, about 22.5, about 24.7, about 30.8, and about 35.3±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.4, about 17.5, about 22.5, and about 24.7±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.4, about 17.5, and about 24.7±0.2 degrees 2θ.

Figure 10:
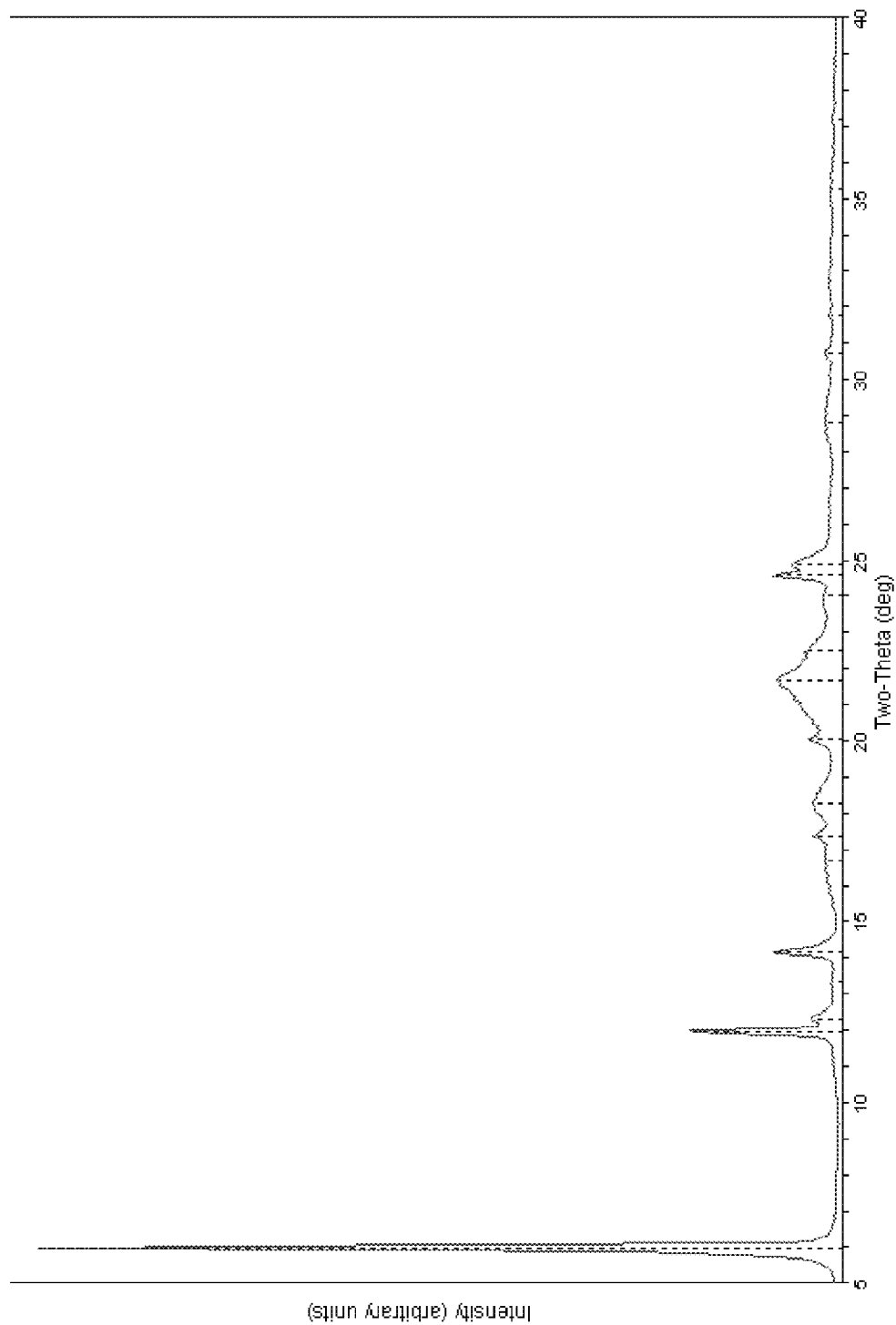
FIG. 10 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 10.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 10.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 11.

TABLE 11

| 2-Theta (°) | d(Å) |
|---|---|
| 5.9 | 14.9 |
| 12.0 | 7.4 |
| 12.3 | 7.2 |
| 14.2 | 6.2 |
| 17.4 | 5.1 |
| 18.4 | 4.8 |
| 20.1 | 4.4 |
| 21.0 | 4.2 |
| 21.8 | 4.1 |
| 22.5 | 3.9 |
| 23.9 | 3.7 |
| 24.6 | 3.6 |
| 25.0 | 3.6 |
| 28.7 | 3.1 |
| 29.2 | 3.1 |
| 30.8 | 2.9 |
| 31.8 | 2.8 |
| 33.6 | 2.7 |
| 35.0 | 2.6 |
| 35.5 | 2.5 |

In some embodiments, a crystalline form of (1S,2R)-2-(amino methyl)-N,N-diethyl-1-phenyl cyclopropane carboxamide is provided having an XRPD pattern comprising one or more peaks at about 12.3, about 17.4, about 20.1, about 22.5, about 24.6, about 29.2, about 30.8, and 33.6±0.2 degrees 2θ. In some embodiments, a crystalline form of (1S, 2R)-2-(amino methyl)-N,N-diethyl-1-phenyl cyclopropane carboxamide is provided having an XRPD pattern comprising one or more peaks at about 12.3, about 17.4, about 20.1, and about 22.5±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 17.4, and about 20.1±0.2 degrees 2θ.

Figure 11:
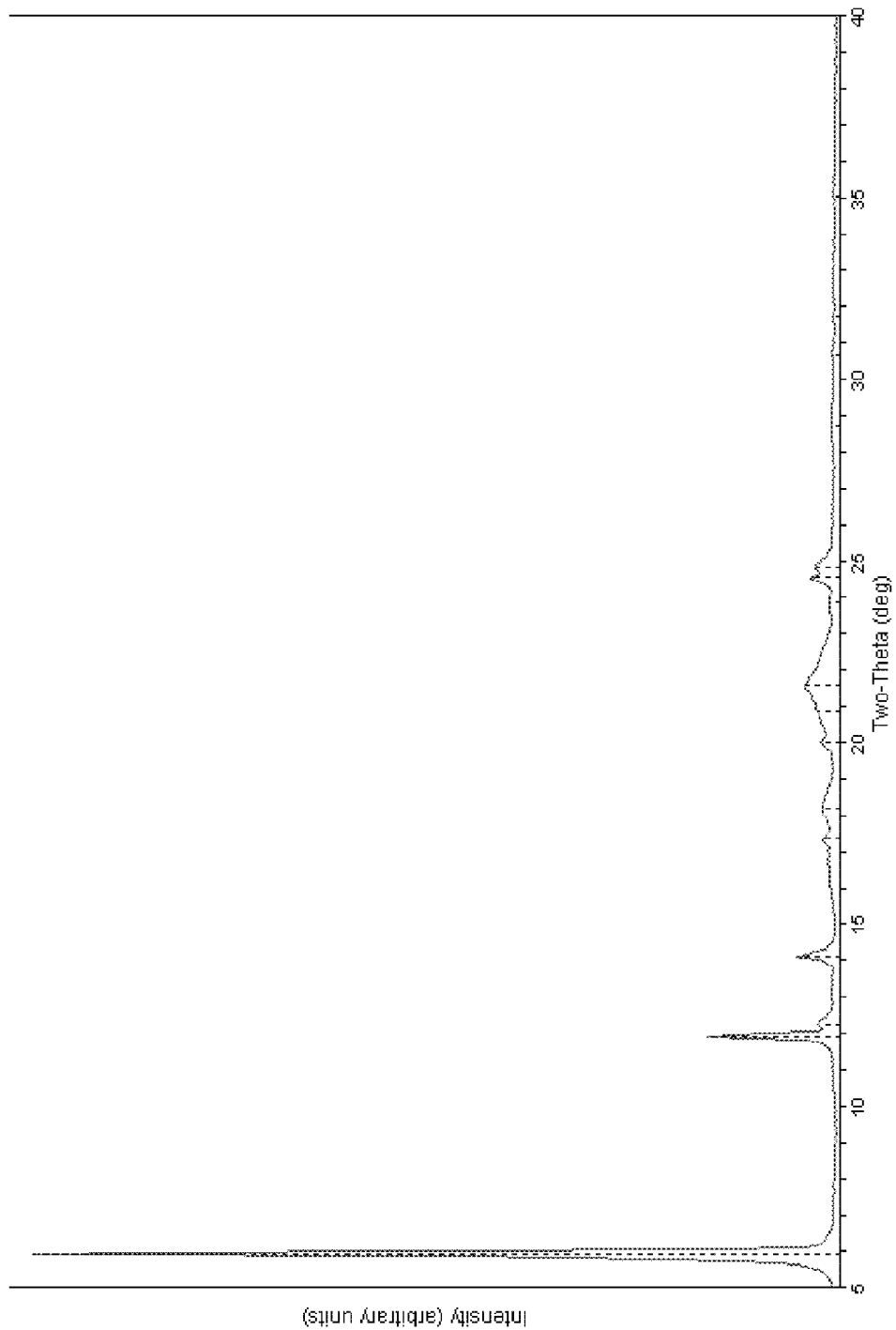
FIG. 11 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 11.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 11.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 12.

TABLE 12

| 2-Theta (°) | d(Å) |
| --- | --- |
| 6.0 | 14.8 |
| 11.9 | 7.4 |
| 12.3 | 7.2 |
| 14.1 | 6.3 |
| 16.6 | 5.3 |
| 17.4 | 5.1 |
| 18.2 | 4.9 |
| 20.0 | 4.4 |
| 21.6 | 4.1 |
| 22.4 | 4.0 |
| 24.5 | 3.6 |
| 24.8 | 3.6 |
| 26.6 | 3.3 |
| 28.8 | 3.1 |
| 30.7 | 2.9 |
| 32.7 | 2.7 |
| 35.1 | 2.6 |

In some embodiments, a crystalline form of (1S,2R)-2-(amino methyl)-N,N-diethyl-1-phenyl cyclopropane carboxamide is provided having an XRPD pattern comprising one or more peaks at about 12.3, about 17.4, about 20.0, about 22.4, about 24.8, about 26.6, about 30.7, about 32.7, and about 35.1±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 17.4, about 20.0, about 22.4, and about 24.8±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 12.3, about 20.0, about 22.4, and about 24.8±0.2 degrees 2θ.

In some embodiments, a crystalline form of (1S,2R)-2-(amino methyl)-N,N-diethyl-1-phenyl cyclopropane carboxamide is provided having an XRPD pattern comprising one or more peaks at about 12.3, about 22.4, and about 24.8±0.2 degrees 2θ. In some embodiments, a crystalline form of (1S,2R)-2-(amino methyl)-N,N-diethyl-1-phenyl cyclopropane carboxamide is provided having an XRPD pattern comprising one or more peaks at about 24.8, about 30.7, about 32.7, and about 35.1±0.2 degrees 2θ.

Figure 12:
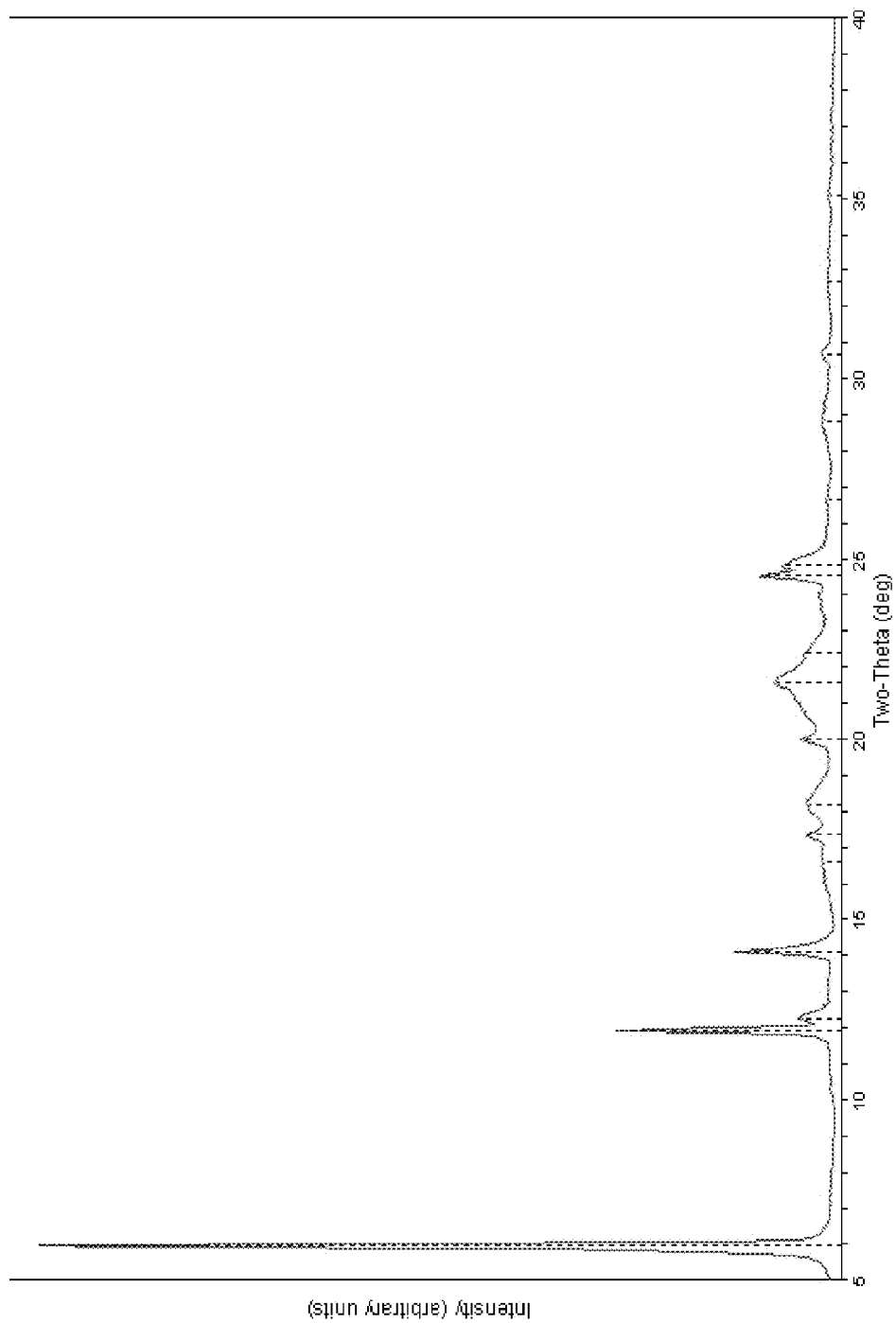
FIG. 12 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 12.

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 12.

Figure 13:
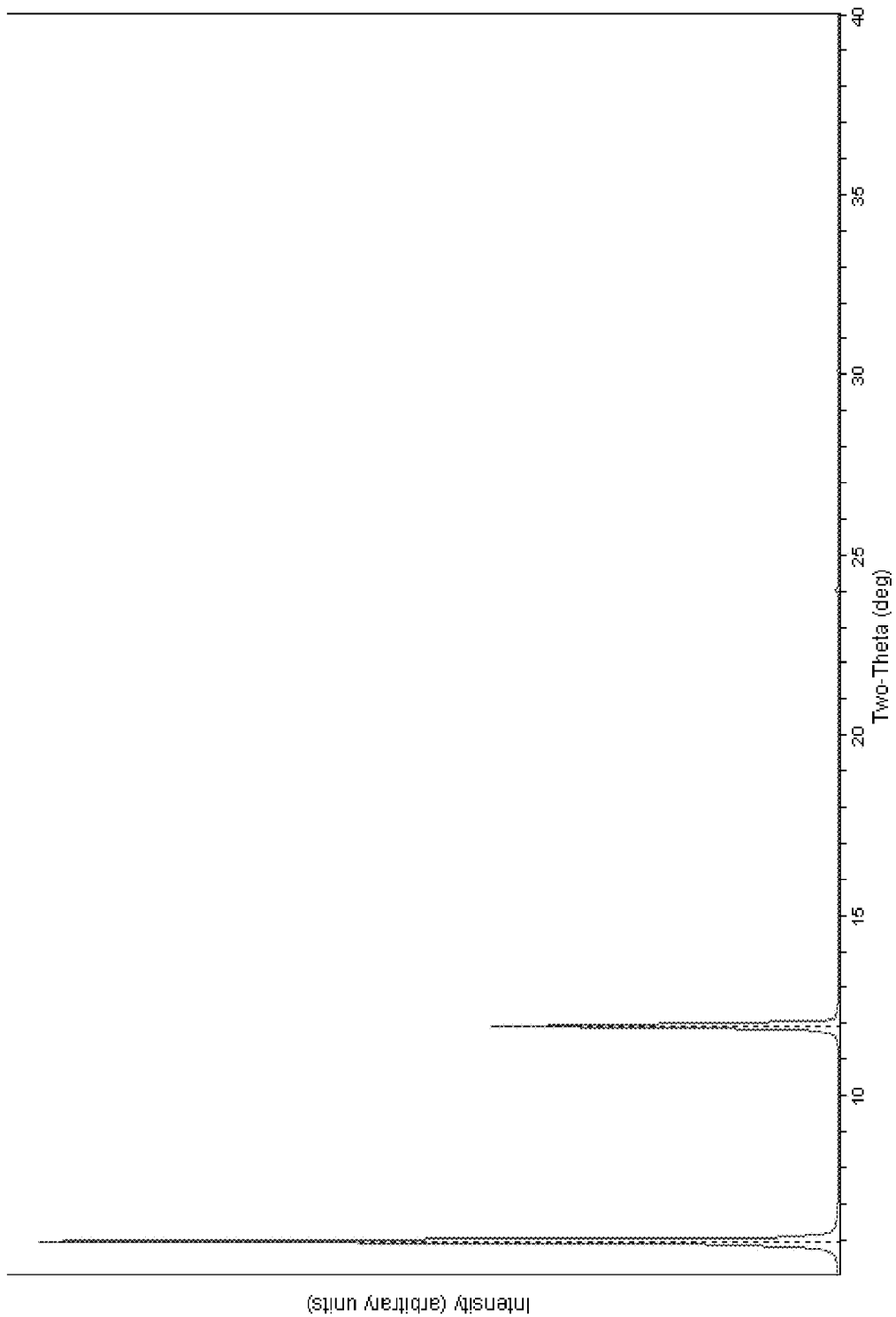
FIG. 13 shows the XRPD pattern of a crystalline form of (1S,2R)-2-(amino methyl)-N,N-diethyl-1-phenyl cyclopropane carboxamide in accordance with an embodiment of the invention.

In some embodiments, a crystalline form of (1S,2R)-2-(amino methyl)-N,N-diethyl-1-phenyl cyclopropane carboxamide is provided, wherein the crystalline form has an XRPD pattern comprising one or more peaks as provided in Table 13. In some embodiments, a crystalline form of (1S,2R)-2-(amino methyl)-N,N-diethyl-1-phenyl cyclopropane carboxamide is provided, wherein the crystalline form is characterized by a XRPD pattern substantially as shown in FIG. 13.

TABLE 13

| 2-Theta (°) | D(Å) |
| --- | --- |
| 6.0 | 14.8 |
| 11.9 | 7.4 |
| 24.0 | 3.7 |
| 30.1 | 3.0 |

In some embodiments, a crystalline form of (1S,2R)-2-(amino methyl)-N,N-diethyl-1-phenyl cyclopropane carboxamide is provided, wherein the crystalline form is characterized by an X-ray diffraction pattern further comprising one or more d spacing peaks as provided in Table 13.

In some embodiments, a crystalline form of (1S,2R)-2-(amino methyl)-N,N-diethyl-1-phenyl cyclopropane carboxamide is provided having an XRPD pattern comprising one or more peaks at about 10.4, about 10.6, about 12.2, about 12.3, about 12.4, about 12.5, about 16.8, about 17.3, about 17.4, about 17.5, about 17.9, about 18.0, about 18.1, about 20.0, about 20.1, about 20.2, about 20.8, about 20.9, about 22.4, about 22.5, about 24.0, about 24.6, about 24.8, about 26.6, about 27.7, about 28.5, about 29.0, about 29.1, about 29.2, about 30.7, about 30.8, about 32.6, about 32.7, about 32.9, about 33.1, about 33.6, about 35.0, about 35.1, about 35.2, about 35.3, about 37.3, about 37.9, about 38.0, about 39.0, about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 10.4±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 10.6±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 12.2±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 12.3±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 12.4±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 12.5±0.2 degrees 2θ. In some embodiments, a crystalline form of (1S,2R)-2-(amino methyl)-N,N-diethyl- 1-phenyl cyclopropane carboxamide is provided having an XRPD pattern comprising a peak at about 16.8±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.3±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.4±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 17.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.9±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 18.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 18.1±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 20.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.1±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.2±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.8±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.9±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 22.4±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 22.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 24.8±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.7±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 26.6±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 27.7±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 28.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 29.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 29.1±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 29.2±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 30.7±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 30.8±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 32.6±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 32.7±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 32.9±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 33.1±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 33.6±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 35.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 35.1±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 35.2±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 35.3±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 37.3±0.2 degrees 2θ. In some embodiments, a crystalline form of (1S,2R)-2-(amino methyl)-N,N-diethyl- 1-phenyl cyclopropane carboxamide is provided having an XRPD pattern comprising a peak at about 37.9±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 38.0±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 39.0±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 12.4±0.2 degrees 2θ and optionally one or more peaks at about 17.4, about 20.1, about 20.8, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4 and about 17.4±0.2 degrees 2θ, and optionally one or more peaks at about 20.1, about 20.8, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4, about 17.4, and about 20.1±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4, about 17.4, about 20.1, and about 24.6±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4, about 17.4, about 20.1, about 24.6, and about 29.1±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4, about 17.4, about 20.1, about 24.6, and about 30.8±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 12.4 and at about 17.4±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 17.4±0.2 degrees 2θ and optionally one or more peaks at about 12.4, about 20.1, about 20.8, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.4±0.2 degrees 2θ, at about 20.1±0.2 degrees 2θ, and optionally one or more peaks at about 12.4, about 20.8, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.4±0.2 degrees 2θ, at about 24.6±0.2 degrees 2θ, and optionally one or more peaks at about 12.4, about 20.1, about 20.8, about 22.4, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.4, about 20.1, and at about 24.6±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 20.1±0.2 degrees 2θ and optionally one or more peaks at about 12.4, about 17.4, about 20.8, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.1±0.2 degrees 2θ, at about 24.6±0.2 degrees 2θ, and optionally one or more peaks at about 12.4, about 17.4, about 20.8, about 22.4, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.1±0.2 degrees 2θ, at about 29.1±0.2 degrees 2θ, and optionally one or more peaks at about 12.4, about 17.4, about 20.8, about 22.4, about 24.6, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 20.1±0.2 degrees 2θ, at about 32.7±0.2 degrees 2θ, and optionally one or more peaks at about 12.4, about 17.4, about 20.8, about 22.4, about 24.6, about 29.1, about 30.8, about 33.1, about 33.6, about 37.3, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 20.8±0.2 degrees 2θ and optionally one or more peaks at about 12.4, about 17.4, about 20.1, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 17.4, at about 20.8±0.2 degrees 2θ, and optionally one or more peaks at about 12.4, about 20.1, about 22.4, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 20.8±0.2 degrees 2θ, about 24.6±0.2 degrees 2θ, and optionally one or more peaks at about 12.4, about 17.4, about 20.1, about 22.4, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 20.8, about 22.4, and about 24.6±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 22.4±0.2 degrees 2θ and optionally one or more peaks at about 12.4, about 17.4, about 20.1, about 20.8, about 24.6, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 22.4±0.2 degrees 2θ, about 24.6±0.2 degrees 2θ, and optionally one or more peaks at about 12.4, about 17.4, about 20.1, about 20.8, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 22.4±0.2 degrees 2θ, about 29.1±0.2 degrees 2θ, and optionally one or more peaks at about 12.4, about 17.4, about 20.1, about 20.8, about 24.6, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 22.4±0.2 degrees 2θ, about 30.8±0.2 degrees 2θ, and optionally one or more peaks at about 12.4, about 17.4, about 20.1, about 20.8, about 24.6, about 29.1, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 22.4±0.2 degrees 2θ, about 32.7±0.2 degrees 2θ, and optionally one or more peaks at about 12.4, about 17.4, about 20.1, about 20.8, about 24.6, about 29.1, about 30.8, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising peaks at about 22.4±0.2 degrees 2θ, about 37.3±0.2 degrees 2θ, and optionally one or more peaks at about 12.4, about 17.4, about 20.1, about 20.8, about 24.6, about 29.1, about 30.8, about 33.1, about 32.7, about 33.6, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ and optionally one or more peaks at about 12.4, about 17.4, about 20.1, about 20.8, about 22.4, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 29.1, about 30.8, about 32.7, about 33.1, about 33.6, about 37.3, about 38.0, about 39.0, and about 41.5±0.2 degrees 2θ, and optionally one or more peaks at about 12.4, about 17.4, about 20.1, about 20.8, about 22.4, about 29.1, about 30.8, about 32.7, about 33.1, about 33.6, about 37.3, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 29.1±0.2 degrees 2θ, and optionally one or more peaks at about 12.4, about 17.4, about 20.1, about 20.8, about 22.4, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 30.8±0.2 degrees 2θ, and optionally one or more peaks at about 12.4, about 17.4, about 20.1, about 20.8, about 22.4, about 29.1, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 32.7±0.2 degrees 2θ, and optionally one or more peaks at about 12.4, about 17.4, about 20.1, about 20.8, about 22.4, about 29.1, about 30.8, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 33.1±0.2 degrees 2θ, and optionally one or more peaks at about 12.4, about 17.4, about 20.1, about 20.8, about 22.4, about 29.1, about 30.8, about 32.7, about 33.6, about 37.3, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 33.6±0.2 degrees 2θ, and optionally one or more peaks at about 12.4, about 17.4, about 20.1, about 20.8, about 22.4, about 29.1, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 37.3±0.2 degrees 2θ, and optionally one or more peaks at about 12.4, about 17.4, about 20.1, about 20.8, about 22.4, about 29.1, about 30.8, about 32.7, about 33.1, about 33.6, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 38.0±0.2 degrees 2θ, and optionally one or more peaks at about 12.4, about 17.4, about 20.1, about 20.8, about 22.4, about 29.1, about 30.8, about 32.7, about 33.1, about 33.6, about 37.3, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 39.0±0.2 degrees 2θ, and optionally one or more peaks at about 12.4, about 17.4, about 20.1, about 20.8, about 22.4, about 29.1, about 30.8, about 32.7, about 33.1, about 33.6, about 37.3, about 38.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 24.6±0.2 degrees 2θ, about 41.5±0.2 degrees 2θ, and optionally one or more peaks at about 12.4, about 17.4, about 20.1, about 20.8, about 22.4, about 29.1, about 30.8, about 32.7, about 33.1, about 33.6, about 37.3, about 38.0, and about 39.0±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 29.1±0.2 degrees 2θ and optionally one or more peaks at about 12.4, about 17.4, about 20.1, about 20.8, about 22.4, about 24.6, about 30.8, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 29.1±0.2 degrees 2θ, about 30.8±0.2 degrees 2θ, and optionally one or more peaks at about 12.4, about 17.4, about 20.1, about 20.8, about 22.4, about 24.6, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 29.1±0.2 degrees 2θ, about 32.7±0.2 degrees 2θ, and optionally one or more peaks at about 12.4, about 17.4, about 20.1, about 20.8, about 22.4, about 24.6, about 30.8, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 29.1±0.2 degrees 2θ, about 37.3±0.2 degrees 2θ, and optionally one or more peaks at about 12.4, about 17.4, about 20.1, about 20.8, about 22.4, about 24.6, about 30.8, about 32.7, about 33.1, about 33.6, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 30.8±0.2 degrees 2θ and optionally one or more peaks at about 12.4, about 17.4, about 20.1, about 20.8, about 22.4, about 24.6, about 29.1, about 32.7, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 30.8±0.2 degrees 2θ, at about 32.7±0.2 degrees 2θ, and optionally one or more peaks at about 12.4, about 17.4, about 20.1, about 20.8, about 22.4, about 24.6, about 29.1, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 30.8±0.2 degrees 2θ, at about 37.3±0.2 degrees 2θ, and optionally one or more peaks at about 12.4, about 17.4, about 20.1, about 20.8, about 22.4, about 24.6, about 29.1, about 32.7, about 33.1, about 33.6, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 32.7±0.2 degrees 2θ and optionally one or more peaks at about 12.4, about 17.4, about 20.1, about 20.8, about 22.4, about 24.6, about 29.1, about 30.8, about 33.1, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 32.7±0.2 degrees 2θ, at about 37.3±0.2 degrees 2θ, and optionally one or more peaks at about 12.4, about 17.4, about 20.1, about 20.8, about 22.4, about 24.6, about 29.1, about 30.8, about 33.1, about 33.6, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 33.1±0.2 degrees 2θ and optionally one or more peaks at about 12.4, about 17.4, about 20.1, about 20.8, about 22.4, about 24.6, about 29.1, about 30.8, about 32.7, about 33.6, about 37.3, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 33.1±0.2 degrees 2θ, at about 37.3±0.2 degrees 2θ, and optionally one or more peaks at about 12.4, about 17.4, about 20.1, about 20.8, about 22.4, about 24.6, about 29.1, about 30.8, about 32.7, about 33.6, about 38.0, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 33.1±0.2 degrees 2θ, at about 38.0±0.2 degrees 2θ, and optionally one or more peaks at about 12.4, about 17.4, about 20.1, about 20.8, about 22.4, about 24.6, about 29.1, about 30.8, about 32.7, about 33.6, about 37.3, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 33.1±0.2 degrees 2θ, at about 41.5±0.2 degrees 2θ, and optionally one or more peaks at about 12.4, about 17.4, about 20.1, about 20.8, about 22.4, about 24.6, about 29.1, about 30.8, about 32.7, about 33.6, about 37.3, about 38.0, and about 39.0±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 33.6±0.2 degrees 2θ and optionally one or more peaks at about 12.4, about 17.4, about 20.1, about 20.8, about 22.4, about 24.6, about 29.1, about 30.8, about 32.7, about 33.1, about 37.3, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 37.3±0.2 degrees 2θ and optionally one or more peaks at about 12.4, about 17.4, about 20.1, about 20.8, about 22.4, about 24.6, about 29.1, about 30.8, about 32.7, about 33.1, about 33.6, about 38.0, about 39.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 38.0±0.2 degrees 2θ and optionally one or more peaks at about 12.4, about 17.4, about 20.1, about 20.8, about 22.4, about 24.6, about 29.1, about 30.8, about 32.7, about 33.1, about 33.6, about 37.3, about 39.0, and about 41.5±0.2 degrees 2θ. In some embodiments, a crystalline form of (1S,2R)-2-(amino methyl)-N,N-diethyl-1-phenyl cyclopropane carboxamide is provided having an XRPD pattern comprising a peak at about 38.0±0.2 degrees 2θ, at about 41.5±0.2 degrees 2θ, and optionally one or more peaks at about 12.4, about 17.4, about 20.1, about 20.8, about 22.4, about 24.6, about 29.1, about 30.8, about 32.7, about 33.1, about 33.6, about 37.3, and about 39.0±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 39.0±0.2 degrees 2θ and optionally one or more peaks at about 12.4, about 17.4, about 20.1, about 20.8, about 22.4, about 24.6, about 29.1, about 30.8, about 32.7, about 33.1, about 33.6, about 37.3, about 38.0, and about 41.5±0.2 degrees 2θ.

In some embodiments, a crystalline form of (1S,2R)-2-(amino methyl)-N,N-diethyl-1-phenyl cyclopropane carboxamide is provided having an XRPD pattern comprising a peak at about 41.5±0.2 degrees 2θ and optionally one or more peaks at about 12.4, about 17.4, about 20.1, about 20.8, about 22.4, about 24.6, about 29.1, about 30.8, about 32.7, about 33.1, about 33.6, about 37.3, about 38.0, and about 39.0±0.2 degrees 2θ.

In some embodiments, the crystalline form of (1S,2R)-2-(amino methyl)-N,N-diethyl-1-phenyl cyclopropane carboxamide has Formula (I).

In some embodiments, the crystalline forms of (1S,2R)-2-(amino methyl)-N,N-diethyl-1-phenyl cyclopropane carboxamide are crystalline forms of (1S,2R)-2-(amino methyl)-N,N-diethyl-1-phenyl cyclopropane carboxamide hydrochloride.

One skilled in the art will understand that 2θ values may change depending on wavelength λ of the X-rays, even as the d-spacing values remain constant.

In some embodiments, the XRPD peaks recited herein for particular embodiments can vary by ±0.05 degrees 2θ, by ±0.1 degrees 2θ, by ±0.3 degrees 2θ, by ±0.4 degrees 2θ, or even by ±0.5 degrees 2θ.

The present invention also provides processes for preparing the crystalline forms of (1S,2R)-2-(amino methyl)-N,N-diethyl-1-phenyl cyclopropane carboxamide.

In some embodiments, a crystalline form of (1S,2R)-2-(amino methyl)-N,N-diethyl-1-phenyl cyclopropane carboxamide may be prepared by a process that comprises mixing (1S,2R)-2-(amino methyl)-N,N-diethyl-1-phenyl cyclopropane carboxamide hydrochloride with a suitable solvent; optionally sonifying and/or heating the mixture; and isolating the crystalline form.

Recrystallization may occur by any of numerous routine methods in the art, such as by cooling or evaporating the solvent to induce precipitation. In one embodiment, after dissolution, crystallization is induced by cooling the mixture. For example, cooling is carried out at a temperature between about −10° C. to about 10° C. In another embodiment, crystals are obtained from a saturated solution at room temperature.

The crystal forms may be dried. For example, drying is carried out at atmospheric pressure (e.g., by allowing the solvent to evaporate), or at reduced pressure (below 1 atm), e.g., below about 100 mm Hg. For example, the drying is carried out at atmospheric pressure and room temperature.

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and deionized water; (ii) maintaining the mixture for a period of time, and (iii) isolating the crystalline form. In some embodiments, the process further comprises sonifying and/or heating the mixture prior to the isolating step.

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and methanol; (ii) maintaining the mixture for a period of time, and (iii) isolating the crystalline form. In some embodiments, the process further comprises sonifying and/or heating the mixture prior to the isolating step. In some embodiments, the mixture is maintained at room temperature in step (ii).

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and ethanol; (ii) maintaining the mixture for a period of time, and (iii) isolating the crystalline form. In some embodiments, the process further comprises sonifying and/or heating the mixture prior to the isolating step. In some embodiments, the mixture is maintained at room temperature in step (ii).

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and isopropanol; (ii) maintaining the mixture for a period of time, and (iii) isolating the crystalline form. In some embodiments, the process further comprises sonifying and/or heating the mixture prior to the isolating step. In some embodiments, the mixture is maintained at room temperature in step (ii).

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and 1-butanol; (ii) maintaining the mixture for a period of time, and (iii) isolating the crystalline form. In some embodiments, the process further comprises sonifying and/or heating the mixture prior to the isolating step. In some embodiments, the mixture is maintained at room temperature in step (ii).

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride dehydrate and a solvent comprising methanol and deionized water; (ii) maintaining the mixture for a period of time, and (iii) isolating the crystalline form. In some embodiments, the process further comprises sonifying and/or heating the mixture prior to the isolating step. In some embodiments, the ratio of water:methanol is from about 90:10 to about 70:30 v/v.; from about 85:15 to about 75:25; from about 80:20 to about 75:25; inclusive of all ranges and sub-ranges therein. In some embodiments, the ratio of water:methanol is from about 10:90 to about 30:70 v/v.; from about 15:85 to about 25:75; from about 20:80 to about 25:75; inclusive of all ranges and sub-ranges therein.

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and a solvent comprising ethylacetate and ethanol; (ii) maintaining the mixture for a period of time, and (iii) isolating the crystalline form. In some embodiments, the process further comprises sonifying and/or heating the mixture prior to the isolating step. In some embodiments, the ratio of ethyl acetate: ethanol is from about 99:1 to about 70:30 v/v.; from about 95:15 to about 25:75; from about 90:10 to about 80:20; inclusive of all ranges and sub-ranges therein. In some embodiments, the mixture is maintained at room temperature in step (ii).

In some embodiments, a crystalline form of (1S,2R)-2-(amino methyl)-N,N-diethyl-1-phenyl cyclopropane carboxamide may be prepared by a process that comprises (i) forming a mixture of (1S,2R)-2-(amino methyl)-N,N-diethyl-1-phenyl cyclopropane carboxamide hydrochloride and a solvent comprising isopropyl alcohol and/or isopropyl acetate and ethanol; (ii) maintaining the mixture for a period of time, and (iii) isolating the crystalline form. In some embodiments, the process further comprises sonifying and/or heating the mixture prior to the isolating step. In some embodiments, the ratio of isopropyl acetate:ethanol is from about 99:1 to about 70:30 v/v.; from about 95:15 to about 25:75; from about 90:10 to about 80:20; inclusive of all ranges and sub-ranges therein. In some embodiments, the mixture is maintained at room temperature in step (ii).

In some embodiments, the crystalline form of (1S,2R)-2-(amino methyl)-N,N-diethyl-1-phenyl cyclopropane carboxamide is isolated in substantially pure form.

In some embodiments, the crystalline form is anhydrous.

One skilled in the art will understand that the relative intensities and positions of the peaks obtained by XRPD and bands obtained by infrared or Raman spectroscopy may vary depending upon, inter alia, the sample preparation technique, the sample mounting procedure and the particular instrument employed.

Compositions

The crystalline forms of (1S,2R)-2-(amino methyl)-N,N-diethyl-1-phenyl cyclopropane carboxamide can be administered alone or as an active ingredient of a formulation. Thus, pharmaceutical compositions comprising, for example, one or more crystalline forms of (1S,2R)-2-(amino methyl)-N,N-diethyl-1-phenyl cyclopropane carboxamide and one or more pharmaceutically acceptable carriers are provided. In addition, pharmaceutical compositions comprising one or more crystalline forms of (1S,2R)-2-(amino methyl)-N,N-diethyl-1-phenyl cyclopropane carboxamide hydrochloride and one or more pharmaceutically acceptable carriers are provided.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the crystalline forms of (1S,2R)-2-(amino methyl)-N,N-diethyl-1-phenyl cyclopropane carboxamide may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering the crystalline forms of (1S,2R)-2-(amino methyl)-N,N-diethyl-1-phenyl cyclopropane carboxamide including such solid forms as tablets, gelcaps, capsules, caplets, granules, lozenges and bulk powders. The crystalline forms of (1S,2R)-2-(amino methyl)-N,N-diethyl-1-phenyl cyclopropane carboxamide can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering the crystalline forms of (1S,2R)-2-(amino methyl)-N,N-diethyl-1-phenyl cyclopropane carboxamide, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The crystalline forms of (1S,2R)-2-(amino methyl)-N,N-diethyl-1-phenyl cyclopropane carboxamide may be injected, for example, intravenously, in the form of an isotonic sterile solution. Other preparations are also possible.

Suppositories for rectal administration of the crystalline forms of (1S,2R)-2-(amino methyl)-N,N-diethyl-1-phenyl cyclopropane carboxamide can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

In some embodiments, the invention provides a composition comprising a crystalline form of a crystalline form of (1S,2R)-2-(amino methyl)-N,N-diethyl-1-phenyl cyclopropane carboxamide.

In some embodiments, a composition is provided having greater than about 0.0001 wt. %, greater than about 0.001 wt. %, greater than about 0.01 wt. %, greater than about 0.1 wt. %, greater than about 0.5 wt. %, greater than about 1 wt. %, greater than about 5 wt. %, greater than about 10 wt. %, greater than about 20 wt. %, greater than about 40 wt. %, greater than about 60 wt. %, greater than about 80 wt. %, greater than about 90 wt. %, greater than about 95 wt. %, or even greater than about 99 wt. %) of one or more crystalline forms of the present invention relative to amorphous form (1S,2R)-2-(amino methyl)-N,N-diethyl-1-phenyl cyclopropane carboxamide and/or other crystalline forms of (1S,2R)-2-(amino methyl)-N,N-diethyl-1-phenyl cyclopropane carboxamide.

In some embodiments, a pharmaceutical composition (e.g., a bead, capsule, or tablet) is provided having greater than about 0.00001-2.0 wt. %, e.g., 0.0001-1.5 wt. %, or even 0.001-1.0 wt. % of one or more crystalline forms of the present invention relative to amorphous form (1S,2R)-2-(amino methyl)-N,N-diethyl-1-phenyl cyclopropane carboxamide and/or other crystalline forms of (1S,2R)-2-(amino methyl)-N,N-diethyl-1-phenyl cyclopropane carboxamide.

The invention also provides the use of a compound of the present invention in the manufacture of a medicament for the treatment of a disorder that can be managed by inhibition of 5-HT and NE reuptake, for example, anxiety disorders or depression (e.g., major depressive disorder).

The present invention further provides methods for treating a disorder that can be managed by inhibition (e.g., double inhibition and/or selective inhibition) of 5-HT and NE reuptake, for example, anxiety disorders or depression (e.g., major depressive disorder) in a mammal (e.g., human) by administering an effective amount of a pharmaceutical composition comprising one or more of the crystalline forms of the present invention to the mammal. In some embodiments, administration of the pharmaceutical composition achieves a ratio of NE reuptake inhibition to 5-HT reuptake inhibition of at least about 2:1.

Disorders that can be managed by inhibition of 5-HT and NE reuptake include, but are not limited to, depression (e.g., major depressive disorder, deep depression, resistant depression, depression in the elderly, psychotic depression, depression induced by treatment with interferon, depressive state, manic-depressive syndrome, seasonal depressive disorder, depressive episodes related to general health status, depressive episodes related to mood-altering substances), anxiety (e.g., generalized anxiety), bi-polar disease, schizophrenia, morose and marasmic states, stress-related diseases, panic attacks, phobias, in particular agoraphobia, obsessive-compulsive disorders, behavioural disorders, oppositional disorders, post-traumatic stress disorder, depression of the immune system, fatigue and accompanying pain syndromes, chronic fatigue syndrome, fibromyalgia, and other functional somatic disorders, autism, disorders characterized by attention deficit due to general health status, attention disorders due to hyperactivity, eating disorders, neurotic bulimia, neurotic anorexia, obesity, psychotic disorders, apathy, migraine, pain and in particular chronic pain, irritable bowel syndrome, cardiovascular diseases and in particular anxiety-depressive syndrome in myocardial infarctus or in hypertension, neurodegenerative diseases and related anxiety-depressive syndromes (Alzheimer's disease, Huntington's chorea, Parkinson's disease), urinary incontinence, in particular urinary incontinence related to stress and enuresis, drug addiction and in particular anxiety addiction to tobacco, in particular to nicotine, to alcohol, to narcotics, to drugs, to analgesics used in weaning-off from these addictive states.

In some embodiments, a pharmaceutical composition comprising one or more crystalline forms of the present invention is administered as a mono-therapy. In other embodiments, a pharmaceutical composition comprising one or more crystalline forms of the present invention is administered as part of a combination therapy. For example, a pharmaceutical composition comprising one or more crystalline forms of the present invention may be used in combination with other drugs or therapies that are used for the treatment, prevention, suppression or amelioration of the diseases or conditions for which compounds of the invention are useful.

Such other drug(s) may be administered, by a route and in an amount commonly used therefore, contemporaneously or sequentially with a pharmaceutical composition comprising one or more crystalline forms of the present invention. When a pharmaceutical composition comprising one or more crystalline forms of the present invention is used contemporaneously with one or more other drugs, the pharmaceutical composition may contain both the crystalline form(s) of the present invention and the other drugs or active ingredients. Accordingly, the pharmaceutical compositions of the present invention include those that also contain one or more other active ingredients, in addition to a compound of invention.

The compounds of the present invention can normally be administered in a daily dosage regimen (for an adult patient) of, for example, an oral dose between 0.1 mg and 500 mg, such as between 1 mg and 400 mg, e.g. between 10 mg and 250 mg. In some embodiments, the active ingredient is administered in an amount of about 0.1 mg, about 0.1, about 1 mg, about 8 mg, about 10 mg, about 20 mg, about 40 mg, about 60 mg, about 80 mg, about 100 mg, about 120 mg, about 140 mg, about 160 mg, about 180 mg, about 200 mg, about 240 mg, about 300 mg, about 360 mg, or even about 480 mg.

The compounds of the present invention can be administered 1 to 4 times per day, for example, once a day, twice a day. The compounds of the present invention can suitably be administered for a period of continuous therapy, for example for a week or more.

Subjects suffering from and in need of treatment of, e.g., depression or any of the other conditions mentioned above can be treated by the administering a therapeutically effective amount of one or more crystalline forms of (1S,2R)-2-(amino methyl)-N,N-diethyl-1-phenyl cyclopropane carboxamide formulated according to, for example and without limitation, the compositions and dosage forms described herein.

Subjects suffering from and in need of treatment of, e.g., schizophrenia, acute mania, and the other conditions mentioned above can be treated by the administering a therapeutically effective amount of a crystalline form of (1S,2R)-2-(amino methyl)-N,N-diethyl-1-phenyl cyclopropane carboxamide formulated according to, for example and without limitation, the compositions and dosage forms described herein.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

As used herein, unless otherwise indicated, the terms "about" and "approximately" should be understood to mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value.

As used herein, unless otherwise indicated, the term "substantially pure" means a composition having a purity greater than, e.g., about 90% by weight, for example, greater than about 91% by weight, greater than about 92% by weight, greater than about 93% by weight, greater than about 94° A) by weight, greater than about 95% by weight, greater than about 96% by weight, greater than about 97% by weight, greater than about 97.5% by weight, greater than about 98% by weight, greater than about 99% by weight, greater than about 99.5% by weight, or greater than about 99.9% by weight.

The term "treating" is used herein, unless otherwise indicated, to mean to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a crystalline form of (1S,2R)-2-(amino methyl)-N,N-diethyl-1-phenyl cyclopropane carboxamide that, when administered to a patient (e.g., human or other mammal) for treating a condition or disorder which may be treated by inhibition of serotonin (5-HT) and norepinephrine (NE) reuptake (e.g., major depressive disorder or anxiety), is sufficient to effect such treatment for the condition or disorder, or an amount of a compound that is sufficient for inhibition of serotonin (5-HT) and norepinephrine (NE) reuptake in a patient. The "effective amount" will vary depending on the compound, the disease and its severity and the age, weight, etc., of the patient to be treated.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

X-Ray Powder Diffractometry (XRD)

A small amount of sample was loaded on a zero background holder and exposed to CuKα radiation (40 kV×40 mA) in a wide-angle bench-top X-ray diffractometer (Model D8, Bruker AXS Inc., Madison Wis.). The instrument was operated in the step-scan mode, in increments of 0.05° 2θ. The angular range was 5 to 40° 2θ, and the scan rate ranged from 1.0-3.5° 2θ/min. The data collection and analyses were performed with commercially available software (JADE, version 7.1, Materials Data, Inc., Livermore, Calif.).

Fourier Transform Raman and IR Spectroscopy (FT-Raman and FT-IR)

For FT-Raman, a small amount of sample (LT 1 mg) was loaded on a glass slide and exposed to Raman laser in a Raman spectrophotometer (Thermo Nicolet Nexus 670 FT-IR/FT-Raman spectrometer, Thermo Electron, Waltham Mass.) using Nicolet EZ Omnic 5.1 software. All spectra were run at 3600-100 $cm^{-1}$ stokes shift, 300 scans and 2 $cm^{-1}$ resolution with laser output between 0.8 and 0.9 watts. For FT-IR, a small amount of sample (LT 1 mg) was loaded onto Durascope™ diamond stage an exposed to an IR beam in the FT-IR spectrometer using attenuated total diffuse reflectance (ATR) mode. All spectra were run at 4000-525 $cm^{-1}$ wave numbers, 16 scans and 2 $cm^{-1}$ resolution.

Differential Scanning Calorimetry (DSC)

A differential scanning calorimeter (MDSC Q1000, TA Instruments, New Castle, Del.) with a refrigerated cooling accessory was used. The instrument was calibrated with pure samples of indium. About 2-5 mg sample was weighed in open non-hermetic aluminum pans with a cover lid and heated under dry nitrogen purge (flow rate 50 ml/min) at 10° C./min. The data was analyzed using Universal Analysis 2000 (TA instruments, New Castle, Del.).

Thermogravimetry (TGA)

A thermogravimetric analyzer (Q5000IR TGA, TA Instruments, New Castle, Del.) with air cooling was used. About 2-10 mg sample was weighed in platinum TGA pans and heated under dry nitrogen purge (flow rate 25 ml/min) at 10° C./min. The data was analyzed using Universal Analysis 2000 (TA instruments, New Castle, Del.).

Example 1

Preparation of Form A (1S,2R)-2-(amino methyl)-N,N-diethyl-1-phenyl cyclopropane carboxamide Form A (1S,2R)-2-(amino methyl)-N,N-diethyl-1-phenyl cyclopropane carboxamide hydrochloride was formed by loading approximately 100 mg of (1S,2R)-2-(amino methyl)-N,N-diethyl-1-phenyl cyclopropane carboxamide hydrochloride into a 10×75 mm culture tube and dissolving it in about 350 mL of ethanol and about 200 mL of ethyl ether. The resulting mixture was heated and sonicated until the (1S,2R)-2-(amino methyl)-N,N-diethyl-1-phenyl cyclopropane carboxamide hydrochloride adequately dissolved into the solvent mixture. The mixture was then carefully filtered (using a 0.45 μm nylon membrane filter) into a separate glass vial and dried with air flow. The product isolated from the vial was Form A (1S,2R)-2-(amino methyl)-N,N-diethyl-1-phenyl cyclopropane carboxamide having the XRPD pattern shown in FIG. 1. Peak positions for the XRPD pattern in FIG. 1 are provided in Table 1.

TABLE 1

| 2-Theta (°) | d(Å) |
|---|---|
| 5.9 | 14.9 |
| 11.9 | 7.4 |
| 24.0 | 3.7 |
| 30.1 | 3.0 |
| 36.3 | 2.5 |

Example 2

Analysis of Crystalline Form of (1S,2R)-2-(amino methyl)-N,N-diethyl-1-phenyl cyclopropane carboxamide A first crystalline form of (1S,2R)-2-(amino methyl)-N,N-diethyl-1-phenyl cyclopropane carboxamide hydrochloride was loaded on a zero background holder and exposed to CuKa radiation (40 kV×40 mA) in a wide-angle bench-top X-ray diffractometer (Model D8, Bruker AXS Inc., Madison Wis.). The instrument was operated in the step-scan mode, in increments of 0.05° 2θ. The angular range was 5 to 40° 2θ, and the scan rate ranged from 1.0-3.5° 2θ/min. The XRPD pattern for the crystalline form is provided in FIG. 2 and peak positions for the XRPD are provided herein in Table 2.

Example 3

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of deionized water was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 3. Peak positions for the XRPD pattern in FIG. 3 are provided herein in Table 3.

Example 4

Preparation of Crystalline Form of (1S,2R)-2-(amino methyl)-N,N-diethyl-1-phenyl cyclopropane carboxamide About 20 mg of (1S,2R)-2-(amino methyl)-N,N-diethyl-1-phenyl cyclopropane carboxamide hydrochloride was weighed into a glass vial. Approximately 1 mL of methanol was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 4. Peak positions for the XRPD pattern in FIG. 4 are provided herein in Table 4.

Example 5

Preparation of Crystalline Form of (1S,2R)-2-(amino methyl)-N,N-diethyl-1-phenyl cyclopropane carboxamide (1S,2R)-2-(amino methyl)-N,N-diethyl-1-phenyl cyclopropane carboxamide hydrochloride was weighed into a glass vial in an quantity of approximately 20 mg. Approximately 1 mL of ethanol was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 5. Peak positions for the XRPD pattern in FIG. 5 are provided herein in Table 5.

Example 6

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 2 mL of isopropanol was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 6. Peak positions for the XRPD pattern in FIG. 6 are provided herein in Table 6.

Example 7

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 3 mL of 1-butanol was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 7. Peak positions for the XRPD pattern in FIG. 7 are provided herein in Table 7.

Example 8

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of N,N dimethyl acetamide was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 8. Peak positions for the XRPD pattern in FIG. 8 are provided herein in Table 8.

Example 9

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of a solvent comprising a ratio of water:acetonitrile of about 80:20 was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 9. Peak positions for the XRPD pattern in FIG. 9 are provided herein in Table 9.

Example 10

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of a solvent comprising a ratio of water:methanol of about 80:20 was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 10. Peak positions for the XRPD pattern in FIG. 10 are provided herein in Table 10.

Example 11

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of a solvent comprising a ratio of water:methanol of about 20:80 was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 11. Peak positions for the XRPD pattern in FIG. 11 are provided herein in Table 11.

Example 12

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 3 mL of dichloromethane was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 12. Peak positions for the XRPD pattern in FIG. 12 are provided herein in Table 12.

Example 13

Preparation of Crystalline Form of (1S,2R)-2-(amino methyl)-N,N-diethyl-1-phenyl cyclopropane carboxamide Approximately 20 mg of (1S,2R)-2-(amino methyl)-N,N-diethyl-1-phenyl cyclopropane carboxamide hydrochloride was weighed into a glass vial. Approximately 1 mL of a solvent comprising a ratio of isopropyl acetate:ethanol of about 90:10 was added to the vial, the vial was capped, and the resulting mixture was heated and sonicated until the (1S,2R)-2-(amino methyl)-N,N-diethyl-1-phenyl cyclopropane carboxamide hydrochloride adequately dissolved into the solvent. The mixture was then carefully filtered (using a 0.2 μm filter) into a separate glass vial and dried on a heater (approx. 30° C.) with air flow. The product isolated from the vial was a crystalline form of (1S,2R)-2-(amino methyl)-N,N-diethyl-1-phenyl cyclopropane carboxamide having the XRPD pattern shown in FIG. 13. Peak positions for the XRPD pattern in FIG. 13 are provided herein in Table 13.

As is demonstrated in the Examples, and as is discussed in this application, the crystalline forms of (1S,2R)-2-(amino methyl)-N,N-diethyl-1-phenyl cyclopropane carboxamide and the crystalline forms of (1S,2R)-2-(amino methyl)-N,N-diethyl-1-phenyl cyclopropane carboxamide hydrochloride may have physical properties (e.g., solid state physical properties) that are surprising and unexpected as compared to amorphous (1S,2R)-2-(amino methyl)-N,N-diethyl-1-phenyl cyclopropane carboxamide and/or other crystalline forms of (1S,2R)-2-(amino methyl)-N,N-diethyl-1-phenyl cyclopropane carboxamide. The crystalline forms of (1S,2R)-2-(amino methyl)-N,N-diethyl-1-phenyl cyclopropane carboxamide and the crystalline forms of (1S,2R)-2-(amino methyl)-N,N-diethyl-1-phenyl cyclopropane carboxamide hydrochloride may also have synergy with other active or inactive components resulting in enhanced performance characteristics or properties of pharmaceutical compositions comprising one or more crystalline forms of the present invention.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure.

The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A crystalline form of (1S,2R)-2-(amino methyl)-N,N-diethyl-1-phenyl cyclopropane carboxamide hydrochloride having an X-ray powder diffraction pattern comprising characteristic peaks at 12.0±0.2 degrees 2θ, 20.1±0.2 degrees 2θ and 22.5±0.2 degrees 2θ.

2. The crystalline form of claim 1, wherein the X-ray powder diffraction pattern further comprises a characteristic peak at 29.2±0.2 degrees 2θ.

3. The crystalline form of claim 1, having a melting endotherm at about 200° C. as determined by differential scanning calorimetry.

4. The crystalline form of claim 1, having a Raman spectrum that comprises characteristic peaks at about 695, about 735 and about 1435 $cm^{-1}$.

5. A pharmaceutical composition comprising a pharmaceutically acceptable carrier and an active ingredient that comprises a crystalline form of (1S,2R)-2-(amino methyl)-N,N-diethyl-1-phenyl cyclopropane carboxamide hydrochloride having an X-ray powder diffraction pattern comprising characteristic peaks at 12.0±0.2 degrees 2θ, 20.1±0.2 degrees 2θ and 22.5±0.2 degrees 2θ.

6. The pharmaceutical composition of claim 5, wherein the X-ray powder diffraction pattern further comprises a characteristic peak at 29.2±0.2 degrees 2θ.

7. The pharmaceutical composition of claim 5, wherein the pharmaceutical composition is a sustained release tablet or capsule that comprises about 20 mg of the active ingredient.

8. The pharmaceutical composition of claim 5, wherein the pharmaceutical composition is a sustained release tablet or capsule that comprises about 40 mg of the active ingredient.

9. The pharmaceutical composition of claim 5, wherein the pharmaceutical composition is a sustained release tablet or capsule that comprises about 80 mg of the active ingredient.

10. The pharmaceutical composition of claim 5, wherein the pharmaceutical composition is a sustained release tablet or capsule that comprises about 120 mg of the active ingredient.

11. The pharmaceutical composition of claim 5, wherein the active ingredient comprises greater than about 20 wt. % of the crystalline form.

12. The pharmaceutical composition of claim 5, wherein the active ingredient comprises greater than about 60 wt. % of the crystalline form.

13. The pharmaceutical composition of claim 5, wherein the active ingredient comprises greater than about 90 wt. % of the crystalline form.

14. A process for preparing a crystalline form of (1S,2R)-2-(amino methyl)-N,N-diethyl-1-phenyl cyclopropane carboxamide hydrochloride, wherein the process comprises dissolving (1S,2R)-2-(amino methyl)-N,N-diethyl-1-phenyl cyclopropane carboxamide hydrochloride in a solvent comprising substantially pure ethanol and precipitating the crystalline form.

15. The process of claim 14, wherein the solvent comprises greater than 96% by weight of ethanol.

16. The process of claim 14, wherein the solvent comprises greater than 98% by weight of ethanol.

17. A crystalline form of (1S,2R)-2-(amino methyl)-N,N-diethyl-1-phenyl cyclopropane carboxamide hydrochloride prepared by the process of any of claims 15-16.

* * * * *